US011008600B2

(12) United States Patent
Ochiai et al.

(10) Patent No.: US 11,008,600 B2
(45) Date of Patent: May 18, 2021

(54) METHOD FOR PRODUCING MOGROL OR MOGROL GLYCOSIDE

(71) Applicant: SUNTORY HOLDINGS LIMITED, Osaka (JP)

(72) Inventors: Misa Ochiai, Kyoto (JP); Eiichiro Ono, Kyoto (JP)

(73) Assignee: SUNTORY HOLDINGS LIMITED, Osaka (JP)

( * ) Notice: Subject to any disclaimer, the term of this patent is extended or adjusted under 35 U.S.C. 154(b) by 153 days.

(21) Appl. No.: 16/318,268

(22) PCT Filed: Jul. 18, 2017

(86) PCT No.: PCT/JP2017/025963
§ 371 (c)(1),
(2) Date: Jan. 16, 2019

(87) PCT Pub. No.: WO2018/016483
PCT Pub. Date: Jan. 25, 2018

(65) Prior Publication Data
US 2019/0284598 A1  Sep. 19, 2019

(30) Foreign Application Priority Data

Jul. 19, 2016  (JP) .............................. JP2016-141685

(51) Int. Cl.
| C12P 19/56 | (2006.01) |
| C12P 7/02 | (2006.01) |
| C12N 9/24 | (2006.01) |
| C12P 19/44 | (2006.01) |
| C12N 15/09 | (2006.01) |
| C12N 5/10 | (2006.01) |
| C12P 19/14 | (2006.01) |

(52) U.S. Cl.
CPC ............... *C12P 19/56* (2013.01); *C12N 5/10* (2013.01); *C12N 9/24* (2013.01); *C12N 15/09* (2013.01); *C12P 7/02* (2013.01); *C12P 19/14* (2013.01); *C12P 19/44* (2013.01)

(58) Field of Classification Search
CPC ........... C12P 19/44; C12P 19/56; C12P 19/14; C12P 7/02; C12N 15/09; C12N 5/10; C12N 9/24; C12Y 302/01021
See application file for complete search history.

(56) References Cited

U.S. PATENT DOCUMENTS

| 2014/0308698 A1 | 10/2014 | Liu et al. |
| 2017/0306289 A1 | 10/2017 | Chung et al. |
| 2018/0010160 A1 | 1/2018 | Ochiai et al. |

FOREIGN PATENT DOCUMENTS

| CN | 102477455 A | 5/2012 | |
| JP | 2014-533518 | 12/2014 | |
| WO | 2011/046768 | 4/2011 | |
| WO | 2013/076577 | 5/2013 | |
| WO | WO-2014081884 A1 * | 5/2014 | ............. A61K 38/16 |
| WO | 2014/150127 | 9/2014 | |
| WO | 2016/053003 A1 | 4/2016 | |
| WO | 2016/117549 | 7/2016 | |

OTHER PUBLICATIONS

Machida, M., Asai, K., Sano, M.etal. Genome sequencing and analysis of Aspergillus oryzae. Nature 438, 1157-1161 (2005). https://doi.org/10.1038/nature04300 (Year: 2005).*
SEQ ID 1 Alignment, SCORE. (Year: 2005).*
SEQ ID 2 Alignment, SCORE. (Year: 2014).*
Extended European Search Report issued in EP Patent Application No. 17830999.3, dated Feb. 21, 2020.
Database UniProt [online], Accession No. Q2U8Y5, http://www.uniprot.org/uniprot/Q2U8Y5.txt?version=60 [retrieved Aug. 7, 2017], (uploaded Jul. 6, 2016).
Chiu et al., "Biotransformation of Mogrosides from *Siraitia grosvenorii* Swingle by *Saccharomyces cerevisiae*", *J. Agric. Food Chem.*, 61(29), pp. 7127-7134 (2013).
Kaya et al., "Isoflavone Aglycones Production from Isoflavone Glycosides by Display of β-glucosidase from *Aspergillus oryzae* on Yeast Cell Surface", *Appl. Microbiol. Biotechnol.*, 79, pp. 51-60 (2008).
Liu et al., "Mogrol Represents a Novel Leukimia Therapeutic, via ERK and STAT3 Inhibition", *Am. J. Cancer Res.*, 5(4), pp. 1308-1318 (2015).
International Search Report issued in PCT/JP2017/025963, dated Aug. 22, 2017, along with an English-language translation.
International Preliminary Report on Patentability issued in PCT/JP2017/025963, dated Jan. 22, 2019, along with an English-language translation.

* cited by examiner

*Primary Examiner* — Satyendra K Singh
(74) *Attorney, Agent, or Firm* — Greenblum & Bernstein, P.L.C.

(57) ABSTRACT

A novel method for producing a mogrol glycoside and mogrol has been required. The present invention provides a method for producing a mogrol glycoside and/or mogrol, said method comprising a step for cleaving at least one glucoside bond in a mogrol glycoside.

15 Claims, 7 Drawing Sheets

Specification includes a Sequence Listing.

[Figure 1A]

```
   1  ATGCCTCGTC TAGACGTGGA GAAGACCATC GAAGAACTCT CCCTAGGGGA GAAGGTCGGC TTGACGGCCG GAATCGACTT CTGGCACACA
      M  P  R  L  D  V  E  K  T  I  E  E  L  S  L  G  E  K  V  A  L  T  A  G  I  D  F  W  H  T

91  GCTTCCGTGC CCCGCCTCAA CATCCCAACT CTCGGCATGT CGGATGGCCC CAACGGCGTG CGCGGAACTG GCTTCTTCAA CGGCGTCCCA
      A  S  V  P  R  L  N  I  P  T  L  R  M  S  D  G  P  N  G  V  R  G  T  R  F  F  N  G  V  P

181  GCCGCATGTT TCCCTTGTGC CACGGCACTG GGCGCAACGT GGGACACCGA GCTGCTCCAT GAGATTGGTG AATTGATGGG AGAGGAATCC
      A  A  C  F  P  C  A  T  A  L  G  A  T  W  D  T  E  L  L  H  E  I  G  G  L  M  G  E  E  S

271  ATTGCCAAGG GCTCGCACAT TATTGTAGGC CCCACGATCA ACACCCAGCG CTCTCGGCTC GGAGGTCGTC GATTCGAGTC CTTTGCTGAG
      I  A  K  G  S  H  I  I  L  G  P  T  I  N  T  Q  R  S  P  L  G  G  R  G  F  E  S  F  A  E

361  GAGGGTGTGC TCTCTGGACT CTTGGCCGGT TATATCTCCA AGGGTATTCA GGAGAAGGGC GTTGCGGCCA CTCTGAAGCA CTTTGTGTGC
      D  G  V  L  S  G  L  L  A  G  Y  I  S  K  G  I  G  E  K  G  V  A  A  T  L  K  H  F  V  G

451  AATGACCAGG AGCATCAGCG TATGGCTGTT GATAGCCATT TTACGCAGCG GGCTCTGCGC GAGATCTATT TGTTGCCGTT TCAATTGGCC
      N  D  Q  E  H  Q  R  M  A  V  D  S  I  V  T  Q  R  A  L  R  E  I  Y  L  L  P  F  Q  L  A

541  ATGAGGATTT GCAGGACGGC TTGTGTTATG ACAGCTTATA ACAAGGTGAA TGGAACGCAC GTTAGTCAGA ATAAGGAAAT CATCACGGAT
      M  R  I  C  R  T  A  C  V  M  T  A  Y  N  K  V  N  G  T  H  V  S  Q  N  K  E  I  I  T  D

631  ATCTTGGGGA AGGAGTGGGG ATGGGATGGG TTGGTTATGA GTGATTGGTT CGGTACGTAC AGTAGCAGTG ATGCAATCAA TGCTGGTTTG
      I  L  R  K  E  W  G  W  D  G  L  V  M  S  D  W  F  G  T  Y  S  T  S  D  A  I  N  A  G  L

721  GAGCTGGAGA TGCCGGGCAA GACAGGCTGG CGTGGAACTG CTCTGGCGCA TGCCGTTTCT TCGAACGAGG TGGCTGAGTT TGTCATGGAT
      D  L  E  M  P  G  K  T  R  W  R  G  I  A  L  A  H  A  V  S  S  N  E  V  A  E  F  V  M  D

811  GAGCGTGTCC GCAATGTGTT GAACCTGGTT AACTTTGTGG ATGGCGTGAA CATCCCGGAG AACGCCCCGG AGAAGGCTCT CAACCCGGCA
      E  R  V  R  N  V  L  N  L  V  N  F  V  D  G  L  N  I  P  E  N  A  P  E  K  A  L  N  R  P

901  CAGGACCAAG GTCTTCTCCG CCGTGCTGCG GGGGAGTGTG TGGTTCTCAT GAAGAACGAG GAAGACATCT TGCCCCTCAA GAAGGAGAAG
      Q  D  Q  A  L  L  R  R  A  A  A  E  S  V  V  L  M  K  N  E  E  D  I  L  P  L  K  K  E  K

991  TCTATCTTGG TTATTGGTCC TAACTCCAAG GTTGCGGCGT ACTGCGGGGG TGGATCGGCG TCTTTGGATG CTTATTACAC TGTCACCCCA
      S  I  L  V  I  G  P  N  S  K  V  A  A  Y  C  G  G  G  S  A  S  L  D  A  Y  Y  T  V  T  P

1081  TTCGAGGGTG TCTCGGCTCA GAGCAAGGGT GAGGTCAAGT TCTCTCAAGG TGTCTATTCG CACAAGGACC TTCCTCTCCT TGGACCCCTG
      F  E  G  V  S  A  Q  S  K  G  E  V  K  F  S  Q  G  V  Y  S  H  K  D  L  P  L  L  G  P  L

1171  CTGAAGACGG CCGACGGCAA GACTGGTTTC TCATTCAAGG TATACAACGA GCACCCTTCC GAGTCTAACC GCGAACTTAT CGAGCAGGTG
      L  K  T  A  D  G  K  T  G  F  S  F  K  V  Y  N  E  H  P  S  E  S  N  R  E  L  I  E  Q  L

1261  CACCTGGTCT CGTCGAGCGG ATTCCTAATG GACTATGTGA ACCCCAAGAT CAAGTCTCTC ACCTACTACG TCGACATGGA GGGTCTCTTC
      H  L  V  S  S  S  G  F  L  M  D  Y  V  N  P  K  I  K  S  L  T  Y  Y  V  D  M  E  G  L  F

1351  ACCCCGGAGG AAGACGGTGT CTACGACTTC GGTGTCAGTG TTGTTGGCAC CGGCCAACTG TTCATCGACG GCGAGCTCGT CGTTGACAAC
      T  P  E  E  D  G  V  Y  D  F  G  V  T  V  V  G  T  G  Q  L  F  I  D  G  E  L  V  V  D  N

1441  ACCAAGAACC AGCGCCAGGG CTCCGCCTTC TTCGGCTCCG CTACCGTCGA AGAGAAGGGC TCCAAAGAAC TCAAGGCCGG CCAAACATAC
      T  K  N  Q  R  Q  G  S  A  F  F  G  S  A  T  V  E  E  K  G  S  K  E  L  K  A  G  Q  I  Y

1531  AAGGTTCTGT TCCAGTTCGG CACAGCCCCT ACCTCCGACC TGGATACCCG CGGCGTGGTA GTCTTCGGAC GCGGTGGCTT CCGCTTCGGA
      K  V  L  F  Q  F  G  T  A  P  T  S  D  L  D  T  R  G  V  V  V  F  G  P  G  G  F  R  F  G

1621  GCCAGCCGTC GCGTCGGCCA GGAAGAGCTC ATCTCCAACG CCGTCAAGCT CGCCTCCGAG GCCGAACAAG TAGTGGTCTT CGCCGGTCTG
      A  S  R  R  V  G  Q  E  E  L  I  S  N  A  V  K  L  A  S  E  A  E  Q  V  V  V  F  A  G  L
```

[Figure 1B]

```
1711    ACTAGCGAAT GGGAAACCGA GGGCTACGAC CGCGACCACA TGGACCTTCC CCCCGGCAGC GACGAGATGA TCTCGCGCGT GCTGGACGTC
         T  S  E  W    E  T  E    G  Y  D    R  G  H  M    D  L  P    P  G  S    D  E  M  I    S  R  V    L  D  V

1801    AAGCCGAAGG CCGTGGTGGT CATTCAGAGC GGCAGGCCAG TGACCATGCC ATGGGCGAAC AAGACCAAGG CTCTCCTACA CGCCTGGTTC
         N  P  A  V  V  V    I  Q  S    G  T  P  V    T  M  P    W  A  N    K  T  K  A    L  L  H  A  W  F

1891    GGCCGTAACG AGTGCGGTAA GGGTATCGCG GACGTGCTGT ACGGCGACGT CAACCCCTCC GGCAAGCTGC CCATTACTTT CCCCGTACGT
         G  G  N  E    C  G  N    G  I  A    D  V  L  Y    G  D  V    N  P  S    G  K  L  P    I  T  F    P  V  R

1981    CTGCAGGACA ACCCCAGCTA CGTCAACTTT CGTTCCGAGC GGGGCCTGT CCTCTACGGT GAAGACGTCT ACGTGGGATA CCGCTACTAC
         L  Q  D  N    P  S  Y    V  N  F    R  S  E  R    G  R  V    L  Y  G    E  D  V  Y    V  G  Y    R  Y  Y

2071    GAAAAGGTGG ATCTGGCCCG TCTCTTCCCG TTCGGCCACG GTCTCTCGTA CACCACGTTC ACCCGCTCGG ACGTGACCGT CACCACCACT
         E  K  V  D    L  A  P    L  F  P    F  G  H  S    L  S  Y    T  T  F    T  R  S  D    L  T  L    T  T  T

2161    CCGGAGAAGC CCCAGTACGA AGAAAGCGGG GAGCCCATCA CCGCAACCGT CACGGTGACC AACACCGGCA AGGTCGCGGG TGCAGAGATC
         P  E  K  P    Q  Y  E    E  S  G    E  P  I  T    A  T  V    T  V  T    N  T  G  K    V  A  G    A  E  I

2251    GTCCAGCTCT GGGTGGCTCC CGCGGCAACG GAAGTCAACG GTCCCGTCCG CGAACTCAAG GGATTCACTA AGGTCTTCCT GCAGCCTGGT
         V  Q  L  W    V  A  P    P  A  T    E  V  N  R    P  V  R    E  L  K    G  F  I  K    V  F  L    Q  P  G

2341    GAGCAGAAGA AGGTCGAGAT CGTCGTGGAG AAGAAGCTGG CGACGAGTTG GTTCGACCAG ATGCGCGAGA AGTGGGCCTC CGAGAAAGGC
         E  Q  K  K    V  E  I    V  V  E    K  K  L  A    T  S  W    F  D  E    M  R  E  K    W  A  S    E  K  G

2431    GAGTATGAGG TTCTTGTAAC TGGTACTGGC GAGGGTGTTC TTAAGTCGTC CTTCAAGGTC GAGAAGACTC GCTACTGGTT GGGTCTGTGA
         E  Y  E  V    L  V  T    G  T  G    E  G  V  L    K  S  S    F  K  V    E  K  T  R    Y  W  L    G  L  *
```

[Figure 3A]

[Figure 3B]
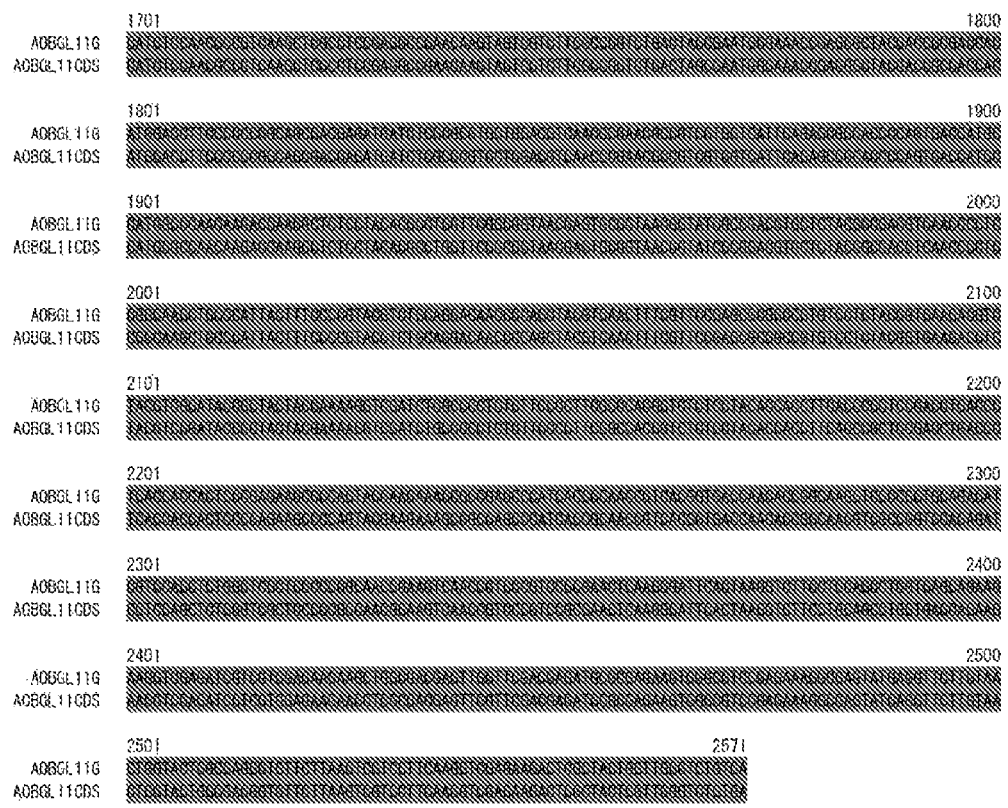

[Figure 4]
A
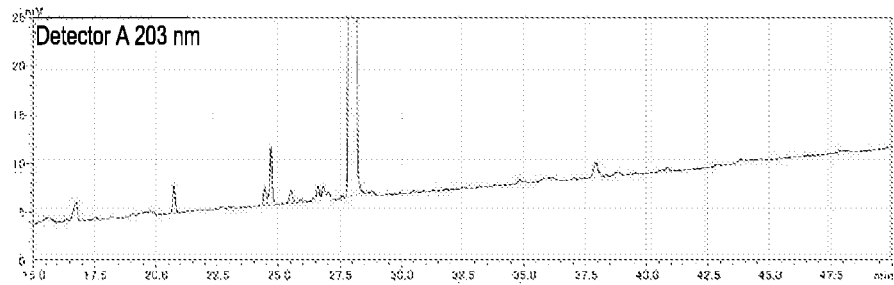
B
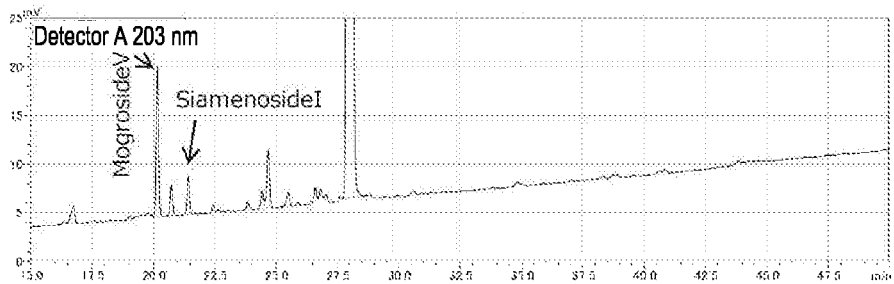
C
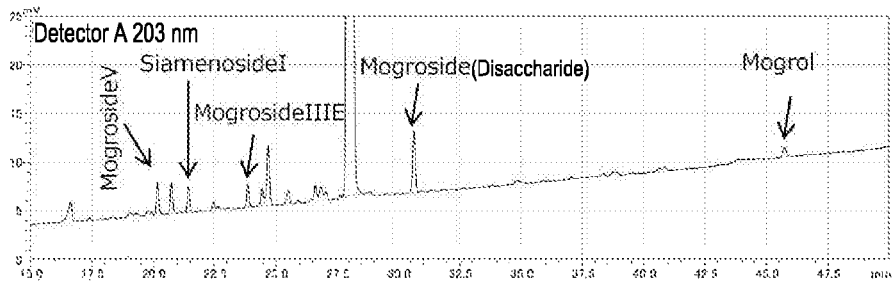
D
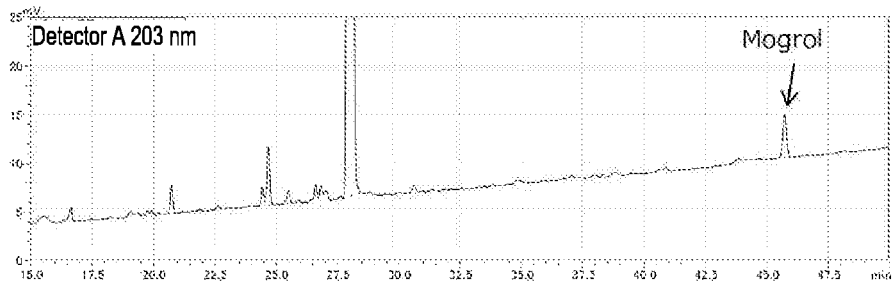

[Figure 5]
A
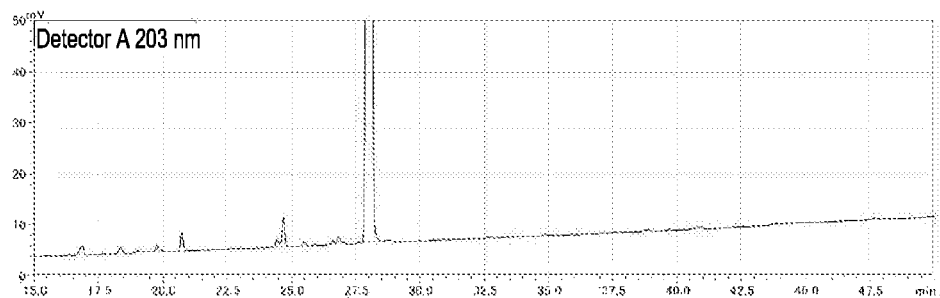
B
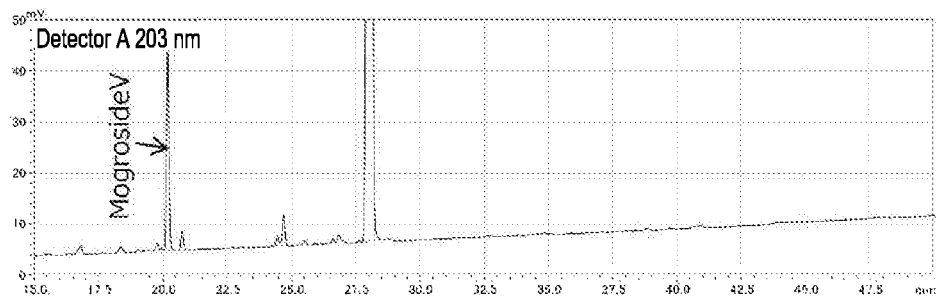

METHOD FOR PRODUCING MOGROL OR MOGROL GLYCOSIDE

TECHNICAL FIELD

The present invention relates to a method for producing mogrol or a mogrol glycoside.

BACKGROUND ART

*Siraitia grosvenorii* is a plant of the Cucurbitaceae family, native to Zhuang Autonomous Region of Guangxi, China. Fruits of *Siraitia grosvenorii* have a very sweet taste, and extracts from the fruits are used as natural sweeteners. Moreover, dried fruits of *Siraitia grosvenorii* are used as Chinese herbal medicines.

Fruits of *Siraitia grosvenorii* are known to contain mogrol glycosides as sweet components. Mogrol glycosides are glycosides wherein glucose is linked to the aglycone, mogrol. Mogrol glycosides are classified into various types of mogrol glycosides according to the linkage position of glucose or the number of glucose units. Mogroside V, mogroside IV, siamenoside I, and 11-oxomogroside are contained as the mogrol glycosides in fruits of *Siraitia grosvenorii*. Other mogrol glycosides are also known, such as mogroside I, mogroside IVA, mogroside III, mogroside IIIA$_1$, mogroside IIIA$_2$, mogroside IIIE, mogroside IIA, mogroside IIA$_1$, mogroside IIA$_2$, mogroside IIB, mogroside IIE, mogroside IA$_1$, and mogroside IE$_1$.

The aglycone, mogrol is known to have an anticancer effect as a bioactive effect (Non Patent Literature 1).

Some methods of preparing mogrol from a mogrol glycoside are known, and, for example, a method comprising heating a mogrol glycoside at 95 to 100° C. for 10 hours in 0.5 N HCl for acid hydrolysis has been disclosed (Non Patent Literature 1).

In addition, a method comprising hydrolyzing a mogrol glycoside with an enzyme is known (Patent Literature 1). In this method, specifically, pectinase derived from *Aspergillus niger* is added and reacted at 50° C. for 48 hours. However, neither the enzyme protein responsible for this activity nor a gene encoding it has been revealed.

It has been disclosed that yeast (*Saccharomyces cerevisiae*) has an activity to convert mogroside V into mogroside IIIE, and the gene of the yeast responsible for this activity is EXG1 (GH family 5, β-1,3-glucanase) (Non Patent Literature 2).

CITATION LIST

Patent Literature

Patent Literature 1: WO2013/076577

Non Patent Literature

Non Patent Literature 1: Am. J. Cancer Res., 5(4), 1308-1318, 2015
Non Patent Literature 2: J. Agric. Food Chem., 61(29), 7127-7134, 2013

SUMMARY OF INVENTION

Technical Problem

Under the foregoing circumstances, there is a need for a novel method of producing mogrol and mogrol glycosides.

Solution to Problem

The present inventors conducted extensive research to solve the aforementioned problem, and found that the koji mold-derived glycoside hydrolase, AOBGL11p, has, for example, an activity to hydrolyze mogroside V into mogrol and a mogrol glycoside, thus completing the present invention.

In summary, the present invention is as set forth below.

(1)

A method of producing mogrol and/or a mogrol glycoside comprising reacting a protein selected from the group consisting of proteins (a) to (c) shown below with a mogrol glycoside, thereby hydrolyzing at least one glucoside bond of said mogrol glycoside:

(a) a protein consisting of the amino acid sequence of SEQ ID NO: 2;

(b) a protein consisting of an amino acid sequence wherein 1 to 83 amino acids have been deleted, substituted, inserted, and/or added in the amino acid sequence of SEQ ID NO: 2, and having an activity to hydrolyze at least one glucoside bond of the mogrol glycoside; and (c) a protein having an amino acid sequence having a sequence identity of 90% or more to the amino acid sequence of SEQ ID NO: 2, and having an activity to hydrolyze at least one glucoside bond of the mogrol glycoside.

(2)

The method according to (1) above, wherein the mogrol glycoside to be reacted with the protein is at least one member selected from the group consisting of mogroside V, mogroside IV, siamenoside I, 11-oxomogroside, mogroside I, mogroside IVA, mogroside III, mogroside IIIA$_1$, mogroside IIIA$_2$, mogroside IIIE, mogroside IIA, mogroside IIA$_1$, mogroside IIA$_2$, mogroside IIB, mogroside IIE, mogroside IA$_1$, and mogroside IE$_1$.

(3)

The method according to (1) or (2) above, wherein the mogrol glycoside is at least one member selected from the group consisting of mogroside V, mogroside IIIE, and siamenoside I.

(4)

The method according to any one of (1) to (3) above, wherein the mogrol glycoside is mogrol V.

(5)

The method according to any one of (1) to (4) above, wherein the at least one glucoside bond is any of a β-1,6-glucoside bond of gentiobiose added to position 3 of mogrol, a glucoside bond between glucose added to position 3 of mogrol and aglycone, mogrol, a β-1,6-glucoside bond of a branched trisaccharide added to position 24 of mogrol, a β-1,6-glucoside bond of gentiobiose added to position 24 of mogrol, a β-1,2-glucoside bond of sophorose added to position 24 of mogrol, and/or a glucoside bond between glucose added to position 24 of mogrol and aglycone, mogrol.

(6)

A method of producing mogrol and/or a mogrol glycoside comprising contacting an enzyme agent from a non-human transformed cell obtained by introducing, into a host cell, a polynucleotide selected from the group consisting of polynucleotides (a) to (e) shown below, with a mogrol glycoside, thereby hydrolyzing at least one glucoside bond of said mogrol glycoside:

(a) a polynucleotide consisting of the nucleotide sequence of SEQ ID NO: 1;
(b) a polynucleotide encoding a protein consisting of the amino acid sequence of SEQ ID NO: 2;
(c) a polynucleotide encoding a protein consisting of an amino acid sequence wherein 1 to 83 amino acids have been deleted, substituted, inserted, and/or added in the amino acid sequence of SEQ ID NO: 2, and having an activity to hydrolyze at least one glucoside bond of the mogrol glycoside;
(d) a polynucleotide encoding a protein having an amino acid sequence having a sequence identity of 90% or more to the amino acid sequence of SEQ ID NO: 2, and having an activity to hydrolyze at least one glucoside bond of the mogrol glycoside; and
(e) a polynucleotide which hybridizes under highly stringent conditions to a polynucleotide consisting of a nucleotide sequence complementary to a polynucleotide consisting of the nucleotide sequence of SEQ ID NO: 1 and which encodes a protein having an activity to hydrolyze at least one glucoside bond of the mogrol glycoside.

(7)
The method according to (6) above, wherein the polynucleotide is inserted into an expression vector.

(8)
The method according to (6) or (7) above, wherein the transformed cell is a transformed koji mold, a transformed yeast, a transformed bacterium, or a transformed plant.

(9)
The method according to any one of (6) to (8) above, wherein the mogrol glycoside to be contacted with the enzyme agent is at least one member selected from the group consisting of mogroside V, mogroside IV, siamenoside I, 11-oxomogroside, mogroside I, mogroside IVA, mogroside III, mogroside IIIA$_1$, mogroside IIIA$_2$, mogroside IIIE, mogroside IIA, mogroside IIA$_1$, mogroside IIA$_2$, mogroside IIB, mogroside IIE, mogroside IA$_1$, and mogroside IE$_1$.

(10)
The method according to any one of (6) to (9) above, wherein the mogrol glycoside is at least one member selected from the group consisting of mogroside V, mogroside IIIE, and siamenoside I.

(11)
The method according to any one of (6) to (10) above, wherein the at least one glucoside bond is any of a β-1,6-glucoside bond of gentiobiose added to position 3 of mogrol, a glucoside bond between glucose added to position 3 of mogrol and aglycone, mogrol, a β-1,6-glucoside bond of a branched trisaccharide added to position 24 of mogrol, a β-1,6-glucoside bond of gentiobiose added to position 24 of mogrol, a β-1,2-glucoside bond of sophorose added to position 24 of mogrol, and/or a glucoside bond between glucose added to position 24 of mogrol and aglycone, mogrol.

(12)
A method of producing mogrol and/or a mogrol glycoside comprising culturing a non-human transformant obtained by introducing a polynucleotide selected from the group consisting of polynucleotides (a) to (e) shown below:
(a) a polynucleotide consisting of the nucleotide sequence of SEQ ID NO: 1;
(b) a polynucleotide encoding a protein consisting of the amino acid sequence of SEQ ID NO: 2;
(c) a polynucleotide encoding a protein consisting of an amino acid sequence wherein 1 to 83 amino acids have been deleted, substituted, inserted, and/or added in the amino acid sequence of SEQ ID NO: 2, and having an activity to hydrolyze at least one glucoside bond of the mogrol glycoside;
(d) a polynucleotide encoding a protein having an amino acid sequence having a sequence identity of 90% or more to the amino acid sequence of SEQ ID NO: 2, and having an activity to hydrolyze at least one glucoside bond of the mogrol glycoside; and
(e) a polynucleotide which hybridizes under highly stringent conditions to a polynucleotide consisting of a nucleotide sequence complementary to a polynucleotide consisting of the nucleotide sequence of SEQ ID NO: 1 and which encodes a protein having an activity to hydrolyze at least one glucoside bond of the mogrol glycoside.

(13)
The method according to (10) above, wherein the polynucleotide is inserted into an expression vector.

(14)
The method according to (12) or (13) above, wherein the transformant is a transformed koji mold, a transformed yeast, a transformed bacterium, or a transformed plant.

(15)
The method according to any one of (12) to (14) above, wherein the at least one glucoside bond is any of a β-1,6-glucoside bond of gentiobiose added to position 3 of mogrol, a β-1,6-glucoside bond of a branched trisaccharide added to position 24 of mogrol, and/or a β-1,2-glucoside bond of a branched trisaccharide added to position 24 of mogrol.

Advantageous Effects of Invention

According to the method of the present invention, there is provided a novel method of producing mogrol and a mogrol glycoside.

Various mogrol glycosides can be produced by selecting reaction conditions. In one embodiment of the present invention, the amount of mogrol and/or a mogrol glycoside produced can be increased by selecting reaction conditions such as enzyme concentrations. According to one embodiment of the present invention, the production amount of a mogrol tetrasaccharide glycoside such as siamenoside I, a mogrol trisaccharide glycoside such as mogroside IIIE, a mogrol disaccharide glycoside, etc. can be selectively increased.

BRIEF DESCRIPTION OF DRAWINGS

FIG. 1A shows the cDNA sequence and the amino acid sequence of AOBGL11.
FIG. 1B shows the cDNA sequence and the amino acid sequence of AOBGL11.
FIG. 3A shows the comparison between the genomic DNA sequence and the cDNA sequence of AOBGL11.
FIG. 3B shows the comparison between the genomic DNA sequence and the cDNA sequence of AOBGL11.
FIG. 4 shows the reaction of a BGL11-1 crude enzyme solution with mogroside V. A: no substrate and no diluted BGL11-1 crude enzyme solution. B: mogroside V added as a substrate and a BGL11-1 crude enzyme solution diluted at a dilution ratio of 100. C: mogroside V added as a substrate and a BGL11-1 crude enzyme solution diluted at a dilution ratio of 10. D: mogroside V added as a substrate and no diluted BGL11-1 crude enzyme solution.

FIG. 5 shows the reaction of a C-1 crude enzyme with mogroside V. A: no substrate. B: mogroside V added as a substrate. The C-1 crude enzyme solution was used without being diluted in any of the cases.

DESCRIPTION OF EMBODIMENTS

Figure 2A:
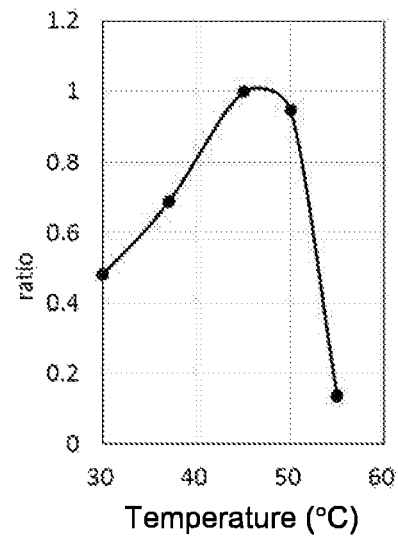
FIG. 2A shows the optimum temperature of AOBGL11p with pNP-β-Glc as a substrate.

The present invention will be hereinafter described in detail. The following embodiments are illustrative of the present invention, and are not intended to limit the present invention. The present invention can be carried out in various manners, without departing from the gist of the invention.

Note that all documents, as well as laid-open application publications, patent application publications, and other patent documents cited herein shall be incorporated herein by reference. The present specification incorporates the contents of the specification and the drawings of Japanese Patent Application No. 2016-141685, filed on Jul. 19, 2016, from which the present application claims priority.

Hereinafter, a mogrol glycoside as a substrate is also referred to as a "substrate mogrol glycoside", and a mogrol glycoside as a product is also referred to as a "produced mogrol glycoside". Both the mogrol glycosides are also collectively referred to as a "mogrol glycoside".

"AOBGL11p" designates a koji mold-derived β-glucosidase; the cDNA sequence, the amino acid sequence, and the genomic DNA sequence thereof are shown in SEQ ID NO: 1, SEQ ID NO: 2, and SEQ ID NO: 3, respectively.

1. Method of Producing Mogrol and/or a Mogrol Glycoside

The present invention provides a method of producing mogrol and/or a mogrol glycoside comprising reacting a protein selected from the group consisting of proteins (a) to (c) shown below (hereinafter referred to as "the protein of the present invention") with a mogrol glycoside, thereby hydrolyzing at least one glucoside bond. In one embodiment, the present invention provides a method of producing mogrol comprising cleaving all glucoside bonds of a mogrol glycoside. In another embodiment, the present invention provides a method of producing mogrol and/or a mogrol glycoside comprising preferentially cleaving a specific bond of a mogrol glycoside, for example, a β-1,6-glucoside bond of gentiobiose added to position 3 of mogrol, and/or a β-1,6-glucoside bond of a branched trisaccharide added to position 24 of mogrol. In this case, the method may comprise cleaving a β-1,2-glucoside bond of the branched trisaccharide, in addition to the β-1,6-glucoside bond.

(a) a protein consisting of the amino acid sequence of SEQ ID NO: 2;

(b) a protein consisting of an amino acid sequence wherein 1 to 83 amino acids have been deleted, substituted, inserted, and/or added in the amino acid sequence of SEQ ID NO: 2, and having an activity to hydrolyze at least one glucoside bond of the mogrol glycoside; and (c) a protein having an amino acid sequence having a sequence identity 90% or more to the amino acid sequence of SEQ ID NO: 2, and having an activity to hydrolyze at least one glucoside bond of the mogrol glycoside.

While the protein shown in (b) or (c) above is typically a variant of a protein consisting of the amino acid sequence of SEQ ID NO: 2, these proteins also include proteins that can be artificially obtained using site-directed mutagenesis as described in, for example, "Sambrook & Russell, Molecular Cloning: A Laboratory Manual Vol. 4, Cold Spring Harbor Laboratory Press 2012", "Ausubel, Current Protocols in Molecular Biology, John Wiley & Sons 1987-1997", "Nuc. Acids. Res., 10, 6487 (1982)", "Proc. Natl. Acad. Sci. USA, 79, 6409 (1982)", "Gene, 34, 315 (1985)", "Nuc. Acids. Res., 13, 4431 (1985)", and "Proc. Natl. Acad. Sci. USA, 82, 488 (1985)".

Examples of the "protein consisting of an amino acid sequence wherein 1 to 83 amino acids have been deleted, substituted, inserted, and/or added in the amino acid sequence of SEQ ID NO: 2, and having an activity to hydrolyze at least one glucoside bond of the mogrol glycoside" include a protein consisting of an amino acid sequence wherein, for example, 1 to 83, 1 to 80, 1 to 75, 1 to 70, 1 to 65, 1 to 60, 1 to 55, 1 to 50, 1 to 49, 1 to 48, 1 to 47, 1 to 46, 1 to 45, 1 to 44, 1 to 43, 1 to 42, 1 to 41, 1 to 40, 1 to 39, 1 to 38, 1 to 37, 1 to 36, 1 to 35, 1 to 34, 1 to 33, 1 to 32, 1 to 31, 1 to 30, 1 to 29, 1 to 28, 1 to 27, 1 to 26, 1 to 25, 1 to 24, 1 to 23, 1 to 22, 1 to 21, 1 to 20, 1 to 19, 1 to 18, 1 to 17, 1 to 16, 1 to 15, 1 to 14, 1 to 13, 1 to 12, 1 to 11, 1 to 10, 1 to 9 (one to several), 1 to 8, 1 to 7, 1 to 6, 1 to 5, 1 to 4, 1 to 3, 1 or 2, or 1 amino acid residue has been deleted, substituted, inserted, and/or added in the amino acid sequence of SEQ ID NO: 2, and having an activity to hydrolyze at least one glucoside bond of a mogrol glycoside. In general, the number of deleted, substituted, inserted, and/or added amino acid residues is preferably smaller.

Examples of such proteins include a protein having an amino acid sequence sharing a sequence identity of 90% or more, 91% or more, 92% or more, 93% or more, 94% or more, 95% or more, 96% or more, 97% or more, 98% or more, 99% or more, 99.1% or more, 99.2% or more, 99.3% or more, 99.4% or more, 99.5% or more, 99.6% or more, 99.7% or more, 99.8% or more, or 99.9% or more with the amino acid sequence of SEQ ID NO: 2, and having an activity to hydrolyze at least one glucoside bond of a mogrol glycoside. In general, the value of sequence identity is preferably greater.

As used herein, the phrase "at least one glucoside bond of the mogrol glycoside" refers to a glucoside bond between aglycone, mogrol and a side chain in a mogrol glycoside, which is a glycoside wherein sugars are linked to mogrol, and a glucoside bond within the side chain. Also, the phrase "activity to hydrolyze at least one glucoside bond of the mogrol glycoside" refers to the activity to cleave (hydrolyze) at least one of a glucoside bond between aglycone, mogrol and a side chain in a mogrol glycoside, which is a glycoside wherein sugars are linked to mogrol, and a glucoside bond within the side chain. Examples of the glucoside bond within the side chain include a β-1,6-glucoside bond of gentiobiose added to position 3 of mogrol, a β-1,6-glucoside bond of a branched trisaccharide at position 24 of mogrol, a β-1,2-glucoside bond of the branched trisaccharide at position 24 of mogrol, a β-1,6-glucoside bond of gentiobiose added to position 24 of mogrol, and/or a β-1,2-glucoside bond of sophorose added to position 24 of mogrol. In an embodiment, all glucoside bonds are hydrolyzed to form mogrol from the mogrol glycoside. In another embodiment, a β-1,6-glucoside bond of gentiobiose added to position 3 of mogrol, and/or a β-1,6-glucoside bond of a branched trisaccharide at position 24 of mogrol is preferentially hydrolyzed. In this way, a mogrol glycoside wherein only some of sugars have been cleaved is formed.

The activity to hydrolyze at least one glucoside bond of the mogrol glycoside can be confirmed by reacting the protein of the present invention with at least one mogrol glycoside selected from the group consisting of, for example, mogroside V, mogroside IV, siamenoside I, 11-oxomogroside, mogroside I, mogroside IVA, mogroside III, mogroside IIIA$_1$, mogroside IIIA$_2$, mogroside IIIE, mogroside IIA, mogroside IIA$_1$, mogroside IIA$_2$, mogroside IIB, mogroside IIE, mogroside IA$_1$, and mogroside IE$_1$, purifying the resulting reaction product (mogrol and/or a mogrol glycoside), and analyzing the purified product using a known technique such as liquid chromatography (LC).

The phrase "an amino acid sequence wherein 1 to 83 amino acid residues have been deleted, substituted, inserted, and/or added in the amino acid sequence of SEQ ID NO: 2" means that 1 to 83 amino acid residues have been deleted, substituted, inserted, and/or added at any 1 to 83 positions in the same sequence, wherein two or more of deletion, substitution, insertion, and addition may occur simultaneously.

Examples of amino acid residues that are interchangeable are shown below. The amino acid residues included in the same group are interchangeable.

Group A: leucine, isoleucine, norleucine, valine, norvaline, alanine, 2-aminobutanoic acid, methionine, o-methylserine, t-butylglycine, t-butylalanine, and cyclohexylalanine;

Group B: aspartic acid, glutamic acid, isoaspartic acid, isoglutamic acid, 2-aminoadipic acid, and 2-aminosuberic acid;

Group C: asparagine and glutamine;

Group D: lysine, arginine, ornithine, 2,4-diaminobutanoic acid, and 2,3-diaminopropionic acid;

Group E: proline, 3-hydroxyproline, and 4-hydroxyproline;

Group F: serine, threonine, and homoserine; and

Group G: phenylalanine and tyrosine.

The protein of the present invention can be obtained by, for example, expressing a polynucleotide encoding this protein (see "the polynucleotide of the present invention" described below) in appropriate host cells, although it can also be produced by a chemical synthesis method such as the Fmoc method (fluorenylmethyloxycarbonyl method) or the tBoc method (t-butyloxycarbonyl method). The protein of the present invention can also be chemically synthesized using a peptide synthesizer from AAPPTec LLC, Perkin Elmer Inc., Protein Technologies Inc., PerSeptive Biosystems, Applied Biosystems, or SHIMADZU CORPORATION, for example.

As used herein, the term "mogrol glycoside" refers to glycoside wherein sugars are linked to mogrol. Examples of mogrol and mogrol glycosides are represented by the following formula (I). Position 3 and position 24 of mogrol are shown in the formula. As used herein, the term "branched trisaccharide" refers to sugars constituting a trisaccharide among those added to the moiety R$_2$ in the following formula (I).

TABLE 1

| Compound name | R$_1$ | R$_2$ | R$_3$ |
|---|---|---|---|
| Mogrol | H | H | H |
| Mogroside V | Glcβ1-6Glcβ1- | Glcβ1-6(Glcβ1-2)Glcβ1- | H |
| Siamenoside I | Glcβ1- | Glcβ1-6(Glcβ1-2)Glcβ1- | H |
| Mogroside IV | Glcβ1-6Glcβ1- | Glcβ1-2Glcβ1- | H |
| Mogroside IVA | Glcβ1-6Glcβ1- | Glcβ1-6Glcβ1- | H |
| Mogroside III | Glcβ1- | Glcβ1-6Glcβ1- | H |
| Mogroside IIIA$_1$ | H | Glcβ1-6(Glcβ1-2)Glcβ1- | H |
| Mogroside IIIA$_2$ | Glcβ1-6Glcβ1- | Glcβ1- | H |
| Mogroside IIIE | Glcβ1- | Glcβ1-2Glcβ1- | H |
| Mogroside IIA | H | Glcβ1-2Glcβ1- | H |
| Mogroside IIA$_1$ | H | Glcβ1-6Glcβ1- | H |
| Mogroside IIA$_2$ | Glcβ1-6Glcβ1- | H | H |
| Mogroside IIB | Glcβ1- | H | Glcβ1- |
| Mogroside IIE | Glcβ1- | Glcβ1- | H |
| Mogroside IA$_1$ | H | Glcβ1- | H |
| Mogroside IE$_1$ | Glcβ1- | H | H |

Examples of mogrol glycosides include mogroside V, mogroside IV, siamenoside I, 11-oxomogroside, mogroside I, mogroside IVA, mogroside III, mogroside IIIA$_1$, mogroside IIIA$_2$, mogroside IIIE, mogroside IIA, mogroside IIA$_1$, mogroside IIA$_2$, mogroside IIB, mogroside IIE, mogroside IA$_1$, and mogroside IE$_1$, although not limited thereto.

In one embodiment of the present invention, a protein consisting of the amino acid sequence of SEQ ID NO: 2 and/or a protein consisting of a variant thereof is used as the enzyme of the present invention. In another embodiment, a mogrol glycoside is available as a substrate. As used herein, examples of mogrol glycosides are as mentioned above. In one embodiment of the present invention, a rare mogrol glycoside such as mogroside IIIE or mogroside II (mogroside IIA, mogroside IIA$_1$, mogroside IIA$_2$, mogroside IIB, mogroside IIE) may be produced with mogroside V, which is a mogrol glycoside most abundantly contained in fruits of *Siraitia grosvenorii*, as a substrate by using the enzyme of the present invention and adjusting the amount of the enzyme added to the reaction, adding an organic solvent into a reaction mixture, or adjusting a reaction temperature, thereby adjusting reaction conditions.

In the present invention, a person skilled in the art will be able to adjust the amount of the enzyme, the substrate/enzyme ratio, the temperature, the pH, the presence or absence of a solvent, the reaction time, etc. of the reaction with a mogrol glycoside as a substrate, as appropriate and able to control the degree of decomposition as to the extent to which sugars linked to the mogrol glycoside are cleaved, by adjusting these factors.

The method of producing mogrol and/or a mogrol glycoside according to the present invention hydrolyzes at least one glucoside bond of the mogrol glycoside.

In the method of producing mogrol and/or a mogrol glycoside according to the present invention, the mogrol glycoside for use as the starting material can be obtained by extraction from *Siraitia grosvenorii* followed by purification using known methods including extraction with an appropriate solvent (an aqueous solvent such as water, or an organic solvent such as an alcohol, ether, or acetone), a gradient between water and ethyl acetate or other organic solvent, high performance liquid chromatography (HPLC), and ultra (high) performance liquid chromatography (UPLC). Alternatively, a commercially-available product may be used as the mogrol glycoside for use as the starting material. The mogrol glycoside for use as the starting material of the present invention includes mogroside V, mogroside IV, siamenoside I, 11-oxomogroside, mogroside I, mogroside IVA, mogroside III, mogroside IIIA$_1$, mogro-

[Formula 1]

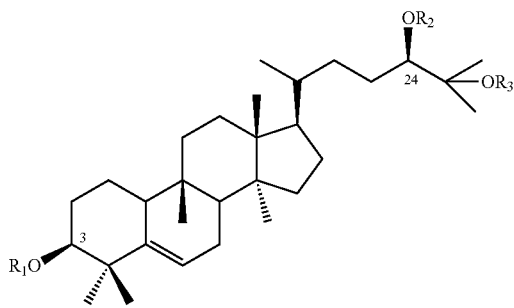

side IIIA$_2$, mogroside IIIE, mogroside IIA, mogroside IIA$_1$, mogroside IIA$_2$, mogroside IIB, mogroside IIE, mogroside IA$_1$, and mogroside IE$_1$ as well as a material that can yield various mogrol glycosides, for example, siamenoside I, mogroside IIIE, and a mogrol disaccharide glycoside, by the cleavage of a β-1,6-glucoside bond or a β-1,2-glucoside bond.

The method of producing mogrol and/or a glycoside mogrol according to the present invention comprises reacting the protein of the present invention with a mogrol glycoside, thereby hydrolyzing said at least one glucoside bond of the mogrol glycoside. The method of the present invention may further comprise purifying the mogrol and/or mogrol glycoside of the present invention which is produced in the above step.

Mogrol and/or the mogrol glycoside according to the present invention can be purified using known methods including extraction with an appropriate solvent (an aqueous solvent such as water, or an organic solvent such as an alcohol, ether, or acetone), a gradient between water and ethyl acetate or other organic solvent, high performance liquid chromatography (HPLC), and ultra (high) performance liquid chromatography (UPLC).

The method of producing a mogrol glycoside and/or mogrol according to the present invention can be performed under conditions where a reaction mixture containing a substrate is supplemented with an organic solvent. The amount of the organic solvent can be in the range of 1% to 20% with respect to the total amount of the reaction mixture and is preferably 5% to 15% or 6 to 12%, more preferably 8%. The organic solvent can be a generally available organic solvent and is preferably an organic solvent for use as a mixture with water at any ratio. Acetonitrile, for example, can be used. The organic solvent may be added to a reaction mixture in advance or may be added during the course of the reaction.

As used herein, the term "polynucleotide" refers to DNA or RNA.

Examples of the polynucleotide encoding the protein consisting of the amino acid sequence of SEQ ID NO: 2 include a polynucleotide consisting of the nucleotide sequence of SEQ ID NO: 1.

Examples of the "protein consisting of an amino acid sequence wherein 1 to 83 amino acids have been deleted, substituted, inserted, and/or added in the amino acid sequence of SEQ ID NO: 2, and having an activity to hydrolyze at least one glucoside bond of a mogrol glycoside" are as described above.

Examples of the "protein having an amino acid sequence having a sequence identity of 90% or more to the amino acid sequence of SEQ ID NO: 2, and having an activity to hydrolyze at least one glucoside bond of a mogrol glycoside" are as described above.

As used herein, the phrase "a polynucleotide which hybridizes under highly stringent conditions" refers to a polynucleotide obtained by means of a hybridization method such as colony hybridization, plaque hybridization, or Southern hybridization, using, as a probe, all of or a portion of a polynucleotide consisting of a nucleotide sequence complementary to the nucleotide sequence of SEQ ID NO: 1 or a polynucleotide consisting of a nucleotide sequence complementary to a nucleotide sequence encoding the amino acid sequence of SEQ ID NO: 2. For hybridization, methods as described in "Sambrook & Russell, Molecular Cloning: A Laboratory Manual Vol. 4, Cold Spring Harbor, Laboratory Press 2012" and "Ausubel, Current Protocols in Molecular Biology, John Wiley & Sons 1987-1997", for example, can be used.

As used herein, the term "highly stringent conditions" refers to, for example, the following conditions: 5×SSC, 5×Denhardt's solution, 0.5% SDS, 50% formamide, 50° C.; 0.2×SSC, 0.1% SDS, 60° C.; 0.2×SSC, 0.1% SDS, 62° C.; or 0.2×SSC, 0.1% SDS, 65° C.; although not limited thereto. Under these conditions, it is expected that DNA having a higher sequence identity will be efficiently obtained at a higher temperature. Note, however, that a plurality of factors such as temperature, probe concentration, probe length, ionic strength, time, and salt concentration are considered to affect the stringency of hybridization, and a person skilled in the art will be able to achieve the same stringency by selecting these factors as appropriate.

When a commercially available kit is used for hybridization, the Alkphos Direct Labelling and Detection System (GE Healthcare), for example, can be used. In this case, hybridization is accomplished in accordance with the protocol attached to the kit, i.e., a membrane may be incubated overnight with a labeled probe and then washed with a primary washing buffer containing 0.1% (w/v) SDS at 55 to 60° C. to detect the hybridized DNA. Alternatively, when a commercially available reagent (e.g., PCR labeling mix (Roche Diagnostics)) is used for digoxigenin (DIG) labeling of a probe during probe preparation based on all of or a portion of a nucleotide sequence complementary to the nucleotide sequence of SEQ ID NO: 1 or a nucleotide sequence complementary to a nucleotide sequence encoding the amino acid sequence of SEQ ID NO: 2, the DIG nucleic acid detection kit (Roche Diagnostics) may be used for detection of hybridization.

In addition to those described above, examples of other hybridizable polynucleotides include DNA sharing 60% or more, 61% or more, 62% or more, 63% or more, 64% or more, 65% or more, 66% or more, 67% or more, 68% or more, 69% or more, 70% or more, 71% or more, 72% or more, 73% or more, 74% or more, 75% or more, 76% or more, 77% or more, 78% or more, 79% or more, 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more, 99% or more, 99.1% or more, 99.2% or more, 99.3% or more, 99.4% or more, 99.5% or more, 99.6% or more, 99.7% or more, 99.8% or more, or 99.9% or more sequence identity with DNA of the nucleotide sequence of SEQ ID NO: 1 or DNA encoding the amino acid sequence of SEQ ID NO: 2, as calculated by the homology search software BLAST using default parameters.

Note that the sequence identity of amino acid sequences or nucleotide sequences can be determined using the BLAST algorithm developed by Karlin and Altschul (Basic Local Alignment Search Tool) (Proc. Natl. Acad. Sci. USA 872264-2268, 1990; Proc Natl Acad Sci USA 90: 5873, 1993). When BLAST is used, default parameters in each program are used.

The above-described polynucleotide of the present invention can be obtained using a known genetic engineering technique or a known synthesis technique.

The polynucleotide of the present invention may further contain a polynucleotide consisting of a nucleotide sequence encoding a secretory signal peptide. Preferably, the polynucleotide of the present invention contains, at its 5' end, the polynucleotide consisting of a nucleotide sequence encoding a secretory signal peptide. The secretory signal peptide and the polynucleotide consisting of a nucleotide sequence encoding the secretory signal peptide are the same as described above.

The polynucleotide of the present invention is preferably inserted into an appropriate expression vector for introduction into a host.

An appropriate expression vector is typically configured to include:

(i) a promoter transcribable in host cells;

(ii) the polynucleotide of the present invention ligated to the promoter; and (iii) an expression cassette containing, as constituent elements, signals that function in the host cells for transcription termination and polyadenylation of an RNA molecule.

Examples of methods for preparing such an expression vector include, although not particularly limited to, using plasmids, phages, cosmids, or the like.

The specific type of the vector is not particularly limited, and any vector expressible in host cells may be selected as appropriate. Specifically, an appropriate promoter sequence may be selected in accordance with the type of the host cells to ensure the expression of the polynucleotide of the present invention, and this promoter sequence and the polynucleotide of the present invention may then be integrated into any of various plasmids, for example, for use as an expression vector.

The expression vector of the present invention contains an expression control region (e.g., a promoter, a terminator, and/or a replication origin), depending on the type of the host into which the expression vector is to be introduced. For bacterial expression vectors, commonly used promoters (e.g., trc promoter, tac promoter, and lac promoter) are used. Examples of yeast promoters include glyceraldehyde-3-phosphate dehydrogenase promoter and PH05 promoter. Examples of filamentous fungi promoters include amylase and trpC. Moreover, examples of promoters for expression of a target gene in plant cells include cauliflower mosaic virus 35S RNA promoter, rd29A gene promoter, rbcS promoter, and mac-1 promoter configured to have the enhancer sequence of the above-mentioned cauliflower mosaic virus 35S RNA promoter at the 5'-side of *Agrobacterium*-derived mannopine synthase promoter sequence. Examples of promoters for animal cell hosts include viral promoters (e.g., SV40 early promoter and SV40 late promoter). Examples of promoters inducibly activated by external stimulation include mouse mammary tumor virus (MMTV) promoter, tetracycline-responsive promoter, metallothionein promoter, and heat-shock protein promoter.

The expression vector preferably contains at least one selection marker. For use as such a marker, auxotrophic markers (ura5, niaD), drug resistance markers (hygromycin, zeocin), geneticin resistance gene (G418r), copper resistance gene (CUP1) (Marin et al., Proc. Natl. Acad. Sci. USA, vol. 81, p. 337, 1984), cerulenin resistance genes (fas2m, PDR4) (Junji Inokoshi et al., Biochemistry, vol. 64, p. 660, 1992; Hussain et al., Gene, vol. 101, p. 149, 1991), and the like are available.

While the method of preparing (producing) the transformant of the present invention is not particularly limited, the transformant of the present invention may be prepared by, for example, introducing an expression vector containing the polynucleotide of the present invention into a host to transform the host. Any of conventionally known various types of cells or organisms can be suitably used as the cells or organism to be transformed. Examples of the cells to be transformed include bacteria such as *Escherichia coli*, yeast (budding yeast *Saccharomyces cerevisiae*, fission yeast *Schizosaccharomyces pombe*), filamentous fungi (koji mold *Aspergillus oryzae, Aspergillus sojae*), plant cells, and non-human animal cells. Appropriate media and conditions for culturing the above-described host cells are well known in the art. Likewise, the organism to be transformed is not particularly limited, and examples include various microorganisms, plants, and non-human animals described above as examples of host cells. The transformant is preferably a filamentous fungus, yeast, or a plant.

The host to be used in transformation can be a host producing any mogrol glycoside. The host that can be used may include not only a plant such as *Siraitia grosvenorii* that originally produces at least one mogrol glycoside, but also a host in which a gene required for the production of at least one mogrol glycoside into cells or an organism that does not originally produce a mogrol glycoside, is introduced. Examples of the "gene required for the production of a mogrol glycoside" include genes having mogrol glycoside synthesis activity such as those described in WO 2016/050890.

For transformation of the host cells, commonly used known methods can be used. For example, transformation can be accomplished using electroporation (Mackenxie, D. A. et al., Appl. Environ. Microbiol., vol. 66, p. 4655-4661, 2000), the particle delivery method (described in JP 2005-287403 A entitled "Breeding Method of Lipid Producing Fungi"), the spheroplast method (Proc. Natl. Acad. Sci. USA, vol. 75, p. 1929, 1978), the lithium acetate method (J. Bacteriology, vol. 153, p. 163, 1983), and other methods as described in Methods in yeast genetics, 2000 Edition: A Cold Spring Harbor Laboratory Course Manual, although not limited thereto. When a gene is introduced into a plant or into tissues or cells from a plant, a method selected from the Agrobacterium method (Plant Molecular Biology Manual, Gelvin, S. B. et al., Academic Press Publishers), particle gun method, PEG method, electroporation, etc. can be used as appropriate.

When the transformant is yeast or koji mold, the yeast or koji mold transformed with the polynucleotide of the present invention expresses a higher level of the protein of the present invention than in the wild-type counterpart. Thus, the expressed protein of the present invention reacts with the mogrol glycoside produced in the yeast or koji mold, the mogrol and/or mogrol glycoside is produced in the cells or culture medium of the yeast or koji mold, preferably in the culture medium.

When the transformant is a plant, the plant to be transformed in the present invention refers to any of whole plants, plant organs (e.g., leaves, petals, stems, roots, and seeds), plant tissues (e.g., epidermis, phloem, parenchyma, xylem, vascular bundles, palisade tissue, and spongy parenchyma) or plant cultured cells, or various forms of plant cells (e.g., suspension cultured cells), protoplasts, leaf sections, calli, and the like. The plant used for transformation may be a plant in the class of either monocotyledons or dicotyledons. The introduction of the polynucleotide of the present invention into the plant can be confirmed by using PCR, Southern hybridization, or Northern hybridization, for example. Once a transformed plant in which the polynucleotide of the present invention has been integrated into the genome is obtained, progeny plants can be produced by sexual or asexual reproduction of the plant. Moreover, seeds, fruits, cuttings, tubers, root tubers, rootstocks, calli, protoplasts or the like can be obtained from this plant or progeny plants thereof, or clones thereof, and used to achieve mass production of the plant. The plant transformed with the polynucleotide of the present invention (hereinafter, "the plant of the present invention") contains a greater amount of the protein of the present invention than in the wild-type counterpart. Thus, the protein of the present invention reacts with the mogrol glycoside produced in the plant of the present invention. As a result, the mogrol is produced in the plant. When the internal environment of the plant is not optimal for hydrolysis reaction, hydrolysis reaction of glucoside bonds of the mogrol glycoside is suppressed. As a result, a mogrol glycoside wherein the glucoside bonds are maintained without being cleaved, or a mogrol glycoside wherein only some of glucoside bonds have been cleaved is produced.

Accordingly, in another embodiment, the present invention provides a method of producing mogrol and/or a mogrol glycoside comprising culturing a non-human transformant in which the polynucleotide of the present invention is introduced.

In some embodiments of the present invention, the transformant or the culture medium thereof has a content of the mogrol and/or the mogrol glycoside of the present invention higher than that in the wild-type counterpart, and an extract or the culture medium of the transformant contains a high concentration of the mogrol and/or the mogrol glycoside of the present invention. An extract of the transformant of the present invention can be obtained by homogenating the transformant with glass beads, a homogenizer, or a sonicator, for example, centrifuging the homogenate, and collecting the supernatant. When the mogrol and/or the mogrol glycoside of the present invention accumulates in the culture medium, the transformant and the culture supernatant may be separated using a standard method (e.g., centrifugation or filtration) after the completion of culture, thereby obtaining the culture supernatant containing the mogrol and/or the mogrol glycoside of the present invention.

The extract or culture supernatant thus obtained may be further subjected to a purification step. The mogrol and/or the mogro glycoside of the present invention may be purified in accordance with a standard separation and purification method. Specific methods for purification are the same as described above.

Method of producing the mogrol glycoside and/or mogrol of the present invention using an enzyme agent from non-human transformed cells The protein of the present invention can be obtained by expressing the protein of the present invention in host cells and homogenating the cells. The mogrol glycoside and/or mogrol of the present invention can also be produced by the action of the protein of the present invention.

Specifically, the mogrol can be produced by contacting an enzyme agent from the transformed cells of the present invention with a mogrol glycoside having at least one glucoside bond. The protein of the present invention has been confirmed in Examples to exhibit equivalent activity both when expressed in yeast and when expressed in koji mold. The "enzyme agent from transformed cells" is not limited as long as it is prepared using transformed cells, and contains the protein of the present invention. Examples of the enzyme agent include transformed cells themselves, a transformed cell homogenate itself, a transformed cell culture supernatant itself, and a purified product thereof. Thus, the present invention provides a method of producing mogrol and/or a mogrol glycoside comprising contacting an enzyme agent from a non-human transformed cell obtained by introducing, into a host cell, a polynucleotide selected from the group consisting of polynucleotides (a) to (e) shown below, with a mogrol glycoside having at least one glucoside bond, thereby hydrolyzing said at least one glucoside bond:

(a) a polynucleotide consisting of the nucleotide sequence of SEQ ID NO: 1;

(b) a polynucleotide encoding a protein consisting of the amino acid sequence of SEQ ID NO: 2;

(c) a polynucleotide encoding a protein consisting of an amino acid sequence wherein 1 to 83 amino acids have been deleted, substituted, inserted, and/or added in the amino acid sequence of SEQ ID NO: 2, and having an activity to hydrolyze at least one glucoside bond of the mogrol glycoside;

(d) a polynucleotide encoding a protein having an amino acid sequence having a sequence identity of 90% or more to the amino acid sequence of SEQ ID NO: 2, and having an activity to hydrolyze at least one glucoside bond of the mogrol glycoside; and (e) a polynucleotide which hybridizes under highly stringent conditions to a polynucleotide consisting of a nucleotide sequence complementary to a polynucleotide consisting of the nucleotide sequence of SEQ ID NO: 1 and which encodes a protein having an activity to hydrolyze at least one glucoside bond of the mogrol glycoside.

The polynucleotide selected from the group consisting of polynucleotides (a) to (e) shown above is the polynucleotide of the present invention, which is the same as described above.

The term "contact" refers to causing the enzyme agent from the transformed cells of the present invention and the mogrol glycoside having at least one glucoside bond to exist in the same reaction or culture system. The term "contact" includes, for example, adding the mogrol glycoside having at least one glucoside bond to a container containing the enzyme agent from the transformed cells of the present invention, mixing the enzyme agent from the transformed cells of the present invention and the mogrol glycoside having at least one glycoside bond, or adding the enzyme agent from the transformed cells of the present invention to a container containing the mogrol glycoside having at least one glucoside bond.

The phrases "mogrol glycoside", "mogrol glycoside having at least one glucoside bond", and "activity to hydrolyze at least one glucoside bond of the mogrol glycoside" are the same as described above.

For other standard molecular biological techniques, reference may be made to "Sambrook & Russell, Molecular Cloning: A Laboratory Manual Vol. 4, Cold Spring Harbor Laboratory Press 2012" and "Methods in Yeast Genetics, A laboratory manual (Cold Spring Harbor Laboratory Press, Cold Spring Harbor, N.Y.)", for example.

The mogrol and/or the mogrol glycoside of the present invention thus obtained can be used for such purposes as the production of foods, sweeteners, flavors, pharmaceutical products, and industrial raw materials (raw materials for cosmetics, soaps, and the like), for example, in accordance with conventional methods.

Examples of foods include nutritional supplements, health foods, functional foods, foods for children, and foods for the elderly. As used herein, the foods refer collectively to edible materials in the form of solids, fluids, liquids, and mixtures thereof.

Note that all documents, as well as laid-open application publications, patent application publications, and other patent documents cited herein shall be incorporated herein by reference.

EXAMPLES

The present invention will be more specifically described hereinafter with reference to examples, which are not intended to limit the scope of the present invention.

Example 1

Search for Koji Mold β-glucosidase Gene

The koji mold genome data (PRJNA28175) was searched for β-glucosidase homologs, and an intracellular β-glucosidase homolog, AO090701000244 (CDS sequence: SEQ ID NO: 1, estimated amino acid sequence: SEQ ID NO: 2, ORF sequence: SEQ ID NO: 3, genomic DNA sequence: SEQ ID NO: 4), is found. This homolog was cloned as AOBGL11. The cDNA sequence and the amino acid sequence of AOBGL11 are shown in FIG. 1.

Cloning of Genomic DNA of AOBGL11

In order to clone AOBGL11, the following primers were designed:

```
AOBGL11-F:
                                        (SEQ ID NO: 4)
5'-ATGCCTCGTCTAGACGTCGAGAA-3'

AOBGL11-R:
                                        (SEQ ID NO: 5)
5'-TCACAGACCCAACCAGTAGCGA-3'
```

Conidia of koji mold *Aspergillus oryzae* var. *Brunneus* (IFO30102) were inoculated to 10 mL of a liquid culture medium (containing, per liter, 20 g of glucose, 1 g of Bacto-tryptone, 5 g of yeast extract, 1 g of NaNO$_3$, 0.5 g of K$_2$HPO$_4$, 0.5 g of MgSO$_4$.7H$_2$O, and 0.01 g of FeSO$_4$.7H$_2$O) and cultured at 30° C. for 1 day. The cells were collected by filtration and ground in liquid nitrogen. Genomic DNA was then prepared using DNeasy Plant Mini Kit (QIAGEN).

Using the genomic DNA as a template, PCR was performed with the primers AOBGL11-F and AOBGL11-R, using KOD-Plus (Toyobo). About 2.57 kbp of the resulting DNA fragment was cloned using the Zero Blunt TOPO PCR cloning Kit (Invitrogen), thus obtaining a plasmid pCR-AOBGL11g.

Example 2

Production of AOBGL11p Using Koji Mold

Construction of Koji Mold Expression Vector

A DNA fragment obtained by digesting a koji mold vector pUNA (National Research Institute of Brewing) with a restriction enzyme SmaI, and approximately 2.57 kbp of a DNA fragment obtained by digesting the plasmid pCR-AOBGL11 g with restriction enzymes EcoRI and blunt-ending the end using Blunting Kit (Takara Bio), were ligated to obtain a plasmid pUNA-AOBGL 11g.

Transformation of Koji Mold

Koji Mold was Transformed as Follows.

*Aspergillus oryzae* niaD300 strain (National Research Institute of Brewing) was used as a host. The host strain was inoculated to a PDA plate and cultured at 30° C. for about 1 week. In order to obtain a conidial suspension, conidia were suspended by adding 0.1% tween 80 and 0.8% NaCl. The suspension was filtered through Miracloth and then centrifuged to collect the conidia. The conidia were then washed with 0.1% tween 80 and 0.8% NaCl and suspended in sterilized water.

The conidia were applied to a CD plate (containing, per liter, 6 g of NaNO$_3$, 0.52 g of KCl, 1.52 g of KH$_2$PO$_4$, 10 g of glucose, 2 mL of 1M MgSO$_4$, 1 mL of a trace element solution (containing, per liter, 1 g of FeSO$_4$.7H$_2$O, 8.8 g of ZnSO$_4$.7H$_2$O, 0.4 g of CuSO$_4$.5H$_2$O, 0.1 g of NaB$_4$O$_7$.10H$_2$O, and 0.05 g of (NH$_4$)$_6$Mo$_7$O$_{24}$.4H$_2$O), and 20 g of agar (pH 6.5)), and DNA was introduced into the conidia by the particle delivery method. This was performed using PDS-1000/He (Bio-Rad), tungsten M-10 particles, and a 1100 psi rupture disc at a distance of 3 cm. A strain that grew on a CD plate was selected as the transformed strain. The strain transformed with the plasmid pUNA-AOBGL11g was designated as BGL11-1 strain, and the strain transformed with the control vector pUNA was designated as C-1 strain.

Expression of AOBGL11p Using Koji Mold

BGL11-1 stain or C-1 strain was inoculated to a CD plate and cultured at 30° C. for 7 days to form conidia. In order to obtain a conidial suspension, the conidia were suspended by adding 0.1% tween 80 and 0.8% NaCl. The suspension was filtered through Miracloth® and then centrifuged to collect the conidia. The conidia were then washed with 0.1% tween 80 and 0.8% NaCl and suspended in sterilized water to prepare a conidial suspension and this conidia suspension was inoculated to a liquid culture medium for enzyme production (containing, per liter, 100 g of maltose, 1 g of Bacto-tryptone, 5 g of yeast extract, 1 g of NaNO$_3$, 0.5 g of K$_2$HPO$_4$, 0.5 g of MgSO$_4$.7H$_2$O, and 0.01 g of FeSO$_4$.7H$_2$O) and cultured with shaking at 30° C. for 2 days. The medium was filtered through Miracloth® to collect the cells. About 4 g of the resulting wet cells was frozen in liquid nitrogen and ground in a mortar. The ground cells were suspended in 50 mM sodium phosphate buffer (pH 7.0), well mixed, and then centrifuged. The resulting supernatant was concentrated by ultrafiltration through Amicon® Ultra-15 50 k (Merck), and the buffer was replaced with 50 mM sodium phosphate buffer (pH 7.0) containing 0.1% CHAPS (buffer A) to obtain about 1 mL of a crude enzyme solution.

Measurement of Protein Concentration

The protein concentration of the crude enzyme solution was determined using Protein Assay CBB Solution (concentrated 5-fold) (Nacalai Tesque). As a result, the protein concentration was 6.46 mg/mL for BGL11-1 crude enzyme solution and 4 mg/mL for C-1 crude enzyme solution.

Example 3 pNP-β-Glc Degrading Activity pNP-β-Glc degrading activity was studied. 10 μL of the crude enzyme solution, 50 μL of a 0.2 M sodium phosphate buffer (pH 7.0), 50 μL of a 20 mM aqueous pNP-β-Glc solution, and water were mixed to a total volume of 200 μL, and the mixture was reacted at 37° C. Since BGL11-1 crude enzyme solution had high activity, the crude enzyme solution was diluted 100-fold with 50 mM sodium phosphate buffer (pH 7.0) containing 0.1% CHAPS and used. The change in absorbance at 405 nm (Δ405) per minute based on p-nitrophenol (pNP) liberated by the hydrolysis of pNP-β-Glc was 0.244 for BGL11-1 crude enzyme solution and 0.000 for C-1 crude enzyme solution.

These results suggested that AOBGL11p is responsible for β-glucosidase activity.

Using pNP-β-Glc as a substrate, AOBGL11p was examined for the optimum temperature, optimum pH, thermal stability, and pH stability (FIG. 2 (FIGS. 2A-2D)).

BGL11-1 crude enzyme solution was diluted 5000-fold with buffer A and used (protein concentration: 1.3 μg/mL).

Optimum Temperature:

The reaction mixture contained 20 µL of the crude enzyme solution (1.3 µg/mL), 100 µL of a 0.2 M sodium phosphate buffer (pH 6.5), 20 mM pNP-β-Glc, and water mixed to a total volume of 400 µL. 15 minutes, 30 minutes, and 45 minutes after the start of reaction, 100 µL was sampled and mixed with 100 µL of a 0.2 M sodium carbonate solution. Then, absorbance at 405 nm was measured, and Δ405 was determined. The ratio of Δ405 from the reaction at each temperature is shown in FIG. 2A, where 45° C. at which the largest value of Δ405 was obtained was defined as 1. These results indicated that 45 to 50° C. is the optimum reaction temperature.

Figure 2B:
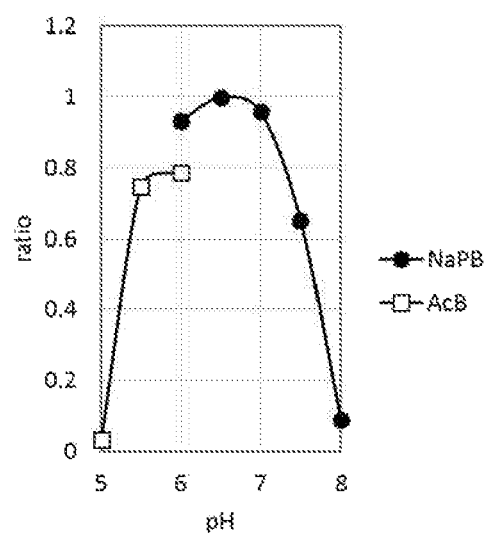
FIG. 2B shows the optimum pH of AOBGL11p with pNP-β-Glc as a substrate.

Optimum pH:

The reaction mixture contained 20 µL of the crude enzyme solution (1.3 µg/mL), 100 µL of a 0.2 M buffer, 20 mM pNP-β-Glc, and water mixed to a total volume of 400 µL. The buffer used was a sodium acetate buffer for pH 4.0 to 6.0 and a sodium phosphate buffer for pH 6.0 to 8.0. Sampling and measurement were performed in the same manner as above. The ratio of Δ405 from the reaction at each pH to the largest value of Δ405 is shown in FIG. 2B. These results indicated that pH 6.0 to 7.0 is the optimum reaction pH.

Figure 2C:
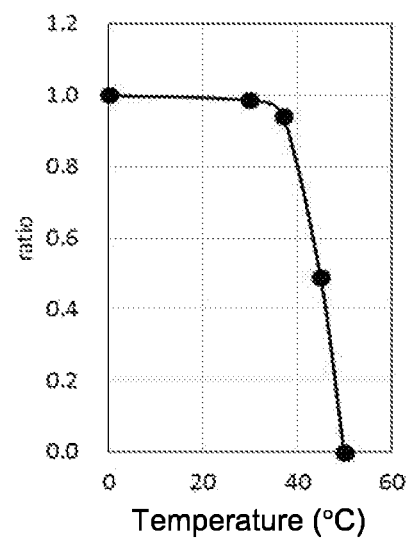
FIG. 2C shows the thermal stability of AOBGL11p with pNP-β-Glc as a substrate.
Figure 2D:
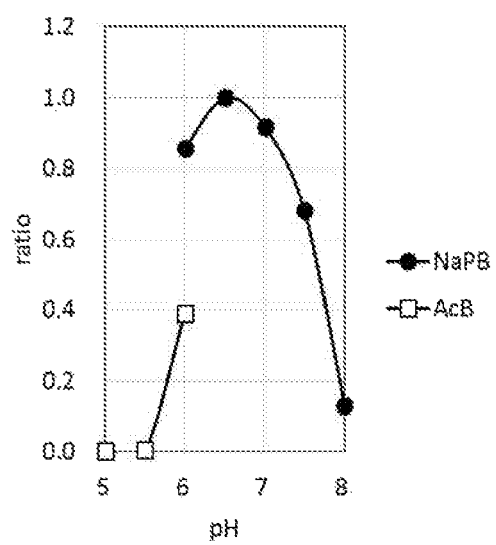
FIG. 2D shows the pH stability of AOBGL11p with pNP-β-Glc as a substrate.

Thermal Stability:

The crude enzyme solution diluted 5000-fold (1.3 µg/mL) was kept at 30° C., 37° C., 45° C., and 50° C. each for 10 minutes and then cooled in ice. The reaction mixture contained 5 µL of the crude enzyme solution (1.3 µg/mL), 100 µL of a 0.2 M sodium phosphate buffer (pH 6.5), 20 mM pNP-β-Glc, and water mixed to a total volume of 100 µL, and was reacted at 37° C. for 45 minutes. Then, 100 µL of a 0.2 M sodium carbonate solution was added to the reaction mixture, and absorbance at 405 nm was measured. The ratio of absorbance at 405 nm from the treatment at each temperature to absorbance at 405 nm after 45 minutes of an enzyme solution that was not heat-treated was determined. The results are shown in FIG. 2C. AOBGL11p was found to be stable up to 37° C. in the treatment for 10 minutes, to lose about half its activity by the treatment at 45° C., and to lose almost all the activity by the treatment at 50° C.

pH Stability:

The crude enzyme solution was diluted 5000-fold with each buffer of pH 4.5, 5.0, 5.5, or 6.0 (0.2 M acetate buffer) or pH 6.0, 6.5, 7.0, 7.5, or 8.0 (0.2 M sodium phosphate buffer), kept at 37° C. for 1 hour, and then cooled in ice. The reaction mixture contained 5 µL of the crude enzyme solution (1.3 µg/mL), 100 µL of a 0.2 M sodium phosphate buffer (pH 6.5), 20 mM pNP-β-Glc, and water mixed to a total volume of 100 µL, and was reacted at 37° C. for 45 minutes. Then, 100 µL of a 0.2 M sodium carbonate solution was added to the reaction mixture, and absorbance at 405 nm was measured. The ratio of absorbance from the crude enzyme solution kept at each pH to absorbance from the crude enzyme solution kept at pH 6.5 that offered the highest activity was determined. The results are shown in FIG. 2D. AOBGL11p was found to be most stable around pH 6.5.

Example 4

Cloning of cDNA of AOBGL11

Figure 3A:
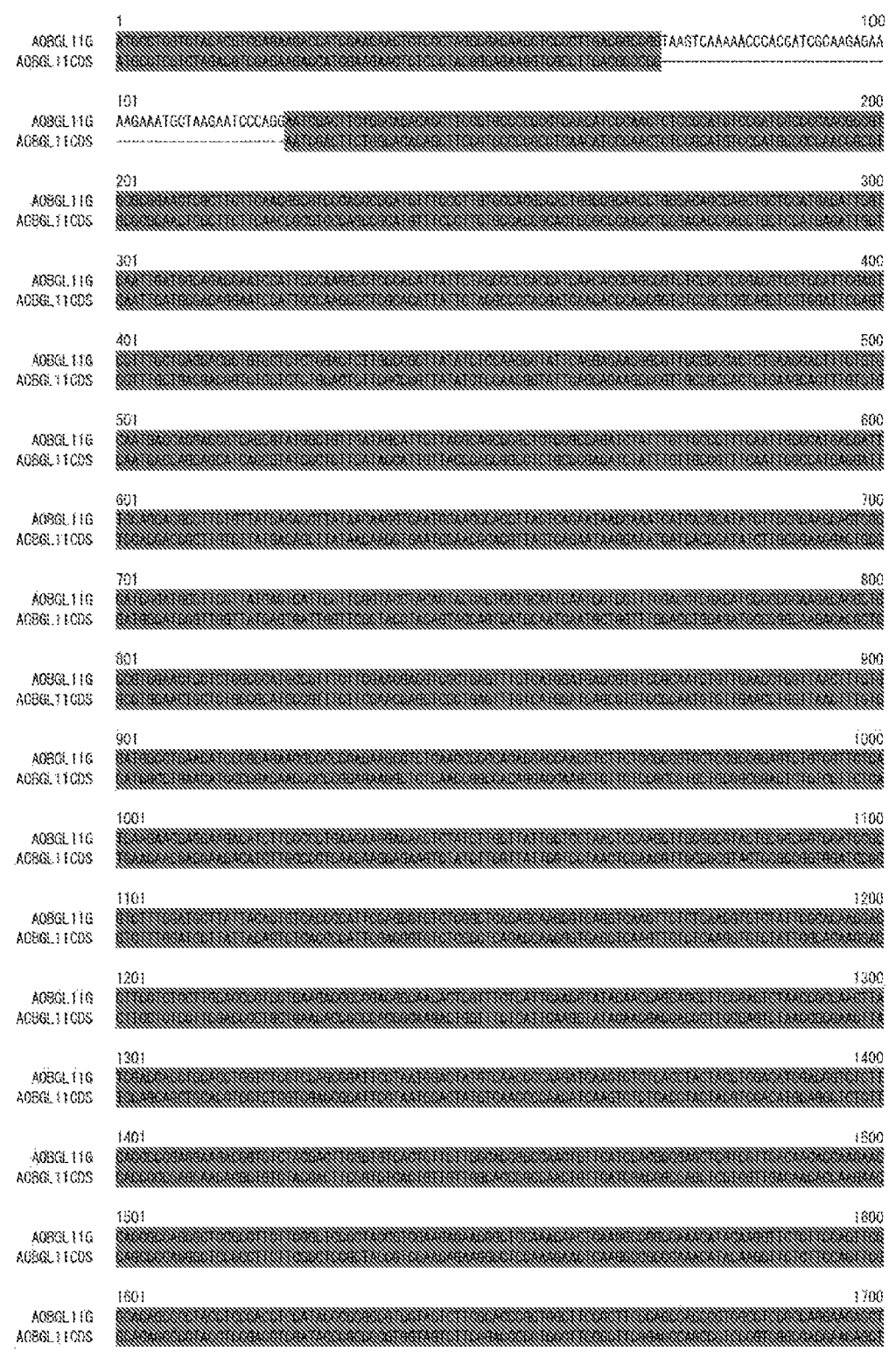

BGL11-1 strain was cultured in 10 mL of a culture medium for enzyme production, and the cells were collected by filtration. The cells were frozen in liquid nitrogen and ground in a mortar, and total RNA was then extracted using RNeasy (QIAGEN). cDNA was synthesized using the SuperScript Double-Stranded cDNA Synthesis Kit (Life Technologies). Using this cDNA as a template, PCR was performed with the primers AOBGL11-F and AOBGL11-R, using KOD-Plus (Toyobo). About 2.52 kbp of the resulting DNA fragment was cloned as AOBGL11 cDNA using the Zero Blunt TOPO PCR cloning Kit (Invitrogen), thus obtaining a plasmid pCR-AOBGL11 cDNA. The nucleotide sequence was confirmed, and was as shown in SEQ ID NO: 1. The comparison between the genomic DNA sequence and the cDNA sequence of AOBGL11 is shown in FIG. 3.

Example 5

Production of AOBGL11p Using Yeast

Construction of Expression Vectors for Yeast and Transformation of Yeast

DNA fragment of about 2.52 kbp obtained by digesting the plasmid pCR-AOBGL11 cDNA with EcoRI was inserted into the EcoRI site of a yeast expression vector pYE22m (Biosci. Biotech. Biochem., 59, 1221-1228, 1995). Expression vector wherein AOBGL11 was inserted in an orientation so as to be expressed under the control of the GAPDH promoter of the vector pYE22m was selected and designated as pYE-AOBGL3c. *S. cerevisiae* strain EH13-15 (trp1, MATα) (Appl. Microbiol. Biotechnol., 30, 515-520, 1989) was used as the parental strain for transformation.

Each of the plasmids pYE22m (control) and pYE-AOBGL11 (for expression of AOBGL11) was used to transform strain EH13-15 in accordance with the lithium acetate method. A strain that grew on SC-Trp (containing, per liter, 6.7 g of Yeast nitrogen base w/o amino acids (DIFCO), 20 g of glucose, and 1.3 g of amino acid powder (a mixture of 1.25 g of adenine sulfate, 0.6 g of arginine, 3 g of aspartic acid, 3 g of glutamic acid, 0.6 g of histidine, 1.8 g of leucine, 0.9 g of lysine, 0.6 g of methionine, 1.5 g of phenylalanine, 11.25 g of serine, 0.9 g of tyrosine, 4.5 g of valine, 6 g of threonine, and 0.6 g of uracil) agar medium (2% agar) was selected as the transformed strain.

The strain transformed with the plasmid pYE22m was designated as C-Y strain, and the strain transformed with the plasmid pYE-AOBGL11 was designated as AOBGL11-Y strain.

One platinum loop of the selected C-Y strain and AOBGL11-Y strain was inoculated to 10 mL of SC-Trp liquid medium supplemented with 1/10 volume of 1 M potassium phosphate buffer, and cultured with shaking at 30° C. and 125 rpm for 2 days. The resulting culture was separated into the culture supernatant and cells by centrifugation. The culture supernatant was concentrated by ultrafiltration through Amicon® Ultra-15 50k (Merck), and the buffer was replaced with 50 mM sodium phosphate buffer (pH 7.0) containing 0.1% CHAPS to obtain about 1 mL of a culture supernatant concentrate.

The cells were suspended in 50 mM sodium phosphate buffer (pH 7.0) containing 0.1% CHAPS solution 1 mL and then homogenated with glass beads, and the supernatant obtained by centrifugation was used as the cell homogenate.

To 20 µL of the culture supernatant concentrate or cell homogenate, 1 µL of a solution of 2% X-β-Glc in DMF was added, and the mixture was reacted at room temperature for 5 minutes. As a result, only the AOBGL11-Y strain-derived cell homogenate was stained blue, suggesting that the strain had X-β-Glc activity.

pNP-β-Glc Activity Measurement pNP-β-Glc degrading activity was studied. 10 µL of the crude enzyme solution, 50 µL of a 0.2 M sodium phosphate buffer (pH 7.0), 50 µL of a 20 mM aqueous pNP-β-Glc solution, and water were mixed to a total volume of 200 µL, and the mixture was reacted at 37° C. Since BGL11-1 crude enzyme solution had high activity, the crude enzyme solution was diluted 100-fold with 50 mM sodium phosphate buffer (pH 7.0) containing 0.1% CHAPS and used. The change in absorbance at 405 nm (Δ405) per minute based on p-nitrophenol (pNP) liberated by the hydrolysis of pNP-β-Glc was 0.068 for the AOBGL11-Y crude enzyme solution and 0.000 for the C-Y crude enzyme solution.

Example 6

Mogrol Glycoside-Hydrolyzing Activity of AOBGL11p Produced Using Koji Mold

Mogroside V was used as a substrate. 50 µg/mL mogroside V, 50 mM sodium phosphate buffer (pH 7.0), and 20 µL of the BGL11-1 crude enzyme solution or a diluted solution thereof were mixed to a total volume of 100 µL, and the mixture was reacted at 37° C. for 1 hour. The C-1 crude enzyme solution was also reacted as described above as a control. The reaction mixture was passed through SepPak C18 500 mg (Waters) washed with methanol and equilibrated with water. The reaction product was washed with 40% methanol and then eluted with 80% methanol. The eluate was evaporated to dryness with SpeedVac. The resulting product was dissolved in 100 µL of water, and the solution was subjected to HPLC.

The analysis conditions for HPLC were as follows:
Column: COSMOSIL 5C$_{18}$-AR-II 4.6 mm I.D.×250 mm (Nacalai Tesque)
Mobile phase: A; acetonitrile, B; water
B conc. 90%→30% 60 min linear gradient
Flow rate: 1 mL/min
Temperature: 40° C.
Detection: UV 203 nm
The results are shown in FIG. 4.

The reaction with the BGL11-1 crude enzyme solution diluted 100-fold hydrolyzed a portion of the substrate mogroside V, thereby producing a mogrol glycoside in the form of a tetrasaccharide. From the retention time, this mogrol glycoside in the form of a tetrasaccharide was considered to be siamenoside I wherein the β-1,6 bond of gentiobiose added to position 3 of mogrol of mogroside V was hydrolyzed.

In the reaction with the enzyme solution diluted 10-fold, the hydrolysis further proceeded, thereby producing mogrol glycosides in the forms of a tetrasaccharide, a trisaccharide (mogroside IIIE from the retention time), and a disaccharide.

In the reaction with the undiluted enzyme solution, neither mogroside V added as a substrate nor glycosides were detected, and aglycone, mogrol was detected.

This demonstrated that the hydrolysis reaction of mogroside V with the BGL11-1 crude enzyme solution proceeds in a manner to cleave glucoses one by one in order so that mogroside V was finally hydrolyzed into the aglycone, mogrol. This also indicates that the progression of hydrolysis of the mogrol glycoside may be controlled by adjusting the concentration of the enzyme solution. The results of reacting the C-1 crude enzyme solution with mogroside V are shown in FIG. 5. These results indicate that the C-1 crude enzyme solution does not allow hydrolysis of mogroside V to proceed.

Example 7

Mogrol Glycoside-Hydrolyzing Activity of AOBGL11p Produced Using Yeast

Cell homogenates of C-Y strain and AOBGL11-Y strain were tested for their activity to hydrolyze mogrol glycosides.

50 µg/mL of a substrate, 20 µL of the enzyme solution, and 50 mM sodium phosphate buffer (pH 6.0) were mixed to a total volume of 100 µL, and the mixture was reacted at 370° C. for 1 hour. The reaction mixture was purified and then subjected to HPLC. The method for purifying the reaction mixture and the conditions for HPLC are as mentioned above.

No product of the reaction using the C-Y strain-derived cell homogenate was detected from any of the mogrol glycosides. On the other hand, use of the AOBGL11-Y strain-derived cell homogenate with mogroside V as a substrate produced siamenoside I, mogroside IIIE, a mogrol disaccharide glycoside, and mogrol as products. These results indicated that when expressed in yeast, AOBGL11 exhibits activity equivalent to the case where AOBGL11 is expressed in koji mold.

INDUSTRIAL APPLICABILITY

The present invention provides a method of producing mogrol and/or a mogrol glycoside by hydrolyzing mogroside V using koji mold-derived glucoside hydrolase, AOBGL11p.

The invention claimed is:

1. A method of producing mogrol and/or a mogrol glycoside comprising reacting a protein selected from the group consisting of proteins (a) to (c) shown below with a substrate mogrol glycoside, under reaction conditions for hydrolyzing at least one glucoside bond of said substrate mogrol glycoside, thereby producing the mogrol and/or mogrol glycoside product:

(a) a protein consisting of the amino acid sequence of SEQ ID NO: 2;
(b) a protein consisting of an amino acid sequence wherein 1 to 83 amino acids have been deleted, substituted, inserted, and/or added in the amino acid sequence of SEQ ID NO: 2, and having an activity to hydrolyze at least one glucoside bond of the substrate mogrol glycoside; and
(c) a protein having an amino acid sequence having a sequence identity of 90% or more to the amino acid sequence of SEQ ID NO: 2, and having an activity to hydrolyze at least one glucoside bond of the substrate mogrol glycoside.

2. The method according to claim 1, wherein the substrate mogrol glycoside to be reacted with the protein is at least one member selected from the group consisting of mogroside V, mogroside IV, siamenoside I, 11-oxomogroside, mogroside I, mogroside IVA, mogroside III, mogroside IIIA1, mogroside IIIA2, mogroside IIIE, mogroside IIA, mogroside IIA1, mogroside IIA2, mogroside IIB, mogroside IIE, mogroside IA1, and mogroside IE1.

3. The method according to claim 2, wherein the substrate mogrol glycoside is at least one member selected from the group consisting of mogroside V, mogroside IIIE, and siamenoside I.

4. The method according to claim 3, wherein the substrate mogrol glycoside is mogroside V.

5. The method according to claim 1, wherein the at least one glucoside bond is any of a β-1,6-glucoside bond of gentiobiose added to position 3 of mogrol, a glucoside bond between glucose added to position 3 of mogrol and aglycone, mogrol, a β-1,6-glucoside bond of a branched trisaccharide added to position 24 of mogrol, a β-1,6-glucoside bond of gentiobiose added to position 24 of mogrol, a β-1,2-glucoside bond of sophorose added to position 24 of mogrol, and/or a glucoside bond between glucose added to position 24 of mogrol and aglycone, mogrol.

6. A method of producing mogrol and/or a mogrol glycoside comprising contacting an enzyme agent from a non-human transformed cell obtained by introducing, into a host cell, a polynucleotide selected from the group consisting of polynucleotides (a) to (d) shown below, with a substrate mogrol glycoside, under reaction conditions for hydrolyzing at least one glucoside bond of said substrate mogrol glycoside, thereby producing the mogrol and/or mogrol glycoside product:

(a) a polynucleotide consisting of the nucleotide sequence of SEQ ID NO: 1;
(b) a polynucleotide encoding a protein consisting of the amino acid sequence of SEQ ID NO: 2;
(c) a polynucleotide encoding a protein consisting of an amino acid sequence wherein 1 to 83 amino acids have been deleted, substituted, inserted, and/or added in the amino acid sequence of SEQ ID NO: 2, and having an activity to hydrolyze at least one glucoside bond of the substrate mogrol glycoside; and
(d) a polynucleotide encoding a protein having an amino acid sequence having a sequence identity of 90% or more to the amino acid sequence of SEQ ID NO: 2, and having an activity to hydrolyze at least one glucoside bond of the substrate mogrol glycoside.

7. The method according to claim 6, wherein the polynucleotide is inserted into an expression vector.

8. The method according to claim 6, wherein the non-human transformed cell is a transformed koji mold, a transformed yeast, a transformed bacterium, or a transformed plant.

9. The method according to claim 6, wherein the substrate mogrol glycoside to be contacted with the enzyme agent is at least one member selected from the group consisting of mogroside V, mogroside IV, siamenoside I, 11-oxomogroside, mogroside I, mogroside IVA, mogroside III, mogroside IIIA$_1$, mogroside IIIA$_2$, mogroside IIIE, mogroside IIA, mogroside IIA$_1$, mogroside IIA$_2$, mogroside IIB, mogroside IIE, mogroside IA$_1$, and mogroside IE$_1$.

10. The method according to claim 9, wherein the substrate mogrol glycoside is at least one member selected from the group consisting of mogroside V, mogroside IIIE, and siamenoside I.

11. The method according to claim 6, wherein the at least one glucoside bond is any of a β-1,6-glucoside bond of gentiobiose added to position 3 of mogrol, a glucoside bond between glucose added to position 3 of mogrol and aglycone, mogrol, a β-1,6-glucoside bond of a branched trisaccharide added to position 24 of mogrol, a β-1,6-glucoside bond of gentiobiose added to position 24 of mogrol, a β-1,2-glucoside bond of sophorose added to position 24 of mogrol, and/or a glucoside bond between glucose added to position 24 of mogrol and aglycone, mogrol.

12. A method of producing mogrol and/or a mogrol glycoside comprising culturing a non-human transformant in which a polynucleotide selected from the group consisting of polynucleotides (a) to (d) shown below is introduced, and contacting an enzyme obtained from said cultured non-human transformant with a substrate mogrol glycoside under reaction conditions for hydrolyzing at least one glucoside bond of said substrate mogrol glycoside, thereby producing the mogrol and/or mogrol glycoside product:
- (a) a polynucleotide consisting of the nucleotide sequence of SEQ ID NO: 1;
- (b) a polynucleotide encoding a protein consisting of the amino acid sequence of SEQ ID NO: 2;
- (c) a polynucleotide encoding a protein consisting of an amino acid sequence wherein 1 to 83 amino acids have been deleted, substituted, inserted, and/or added in the amino acid sequence of SEQ ID NO: 2, and having an activity to hydrolyze at least one glucoside bond of the substrate mogrol glycoside; and
- (d) a polynucleotide encoding a protein having an amino acid sequence having a sequence identity 90% or more to the amino acid sequence of SEQ ID NO: 2, and having an activity to hydrolyze at least one glucoside bond of the substrate mogrol glycoside.

13. The method according to claim 12, wherein the polynucleotide is inserted into an expression vector.

14. The method according to claim 12, wherein the non-human transformant is a transformed koji mold, a transformed yeast, a transformed bacterium or a transformed plant.

15. The method according to claim 12, wherein the at least one glucoside bond is any of a β-1,6-glucoside bond of gentiobiose added to position 3 of mogrol, a glucoside bond between glucose added to position 3 of mogrol and aglycone, mogrol, a β-1,6-glucoside bond of a branched trisaccharide added to position 24 of mogrol, a β-1,6-glucoside bond of gentiobiose added to position 24 of mogrol, a β-1,2-glucoside bond of sophorose added to position 24 of mogrol, and/or a glucoside bond between glucose added to position 24 of mogrol and aglycone, mogrol.

* * * * *

SEQUENCE LISTING

```
<160> NUMBER OF SEQ ID NOS: 5

<210> SEQ ID NO 1
<211> LENGTH: 2520
<212> TYPE: DNA
<213> ORGANISM: Aspergillus oryzae
<220> FEATURE:
<221> NAME/KEY: CDS
<222> LOCATION: (1)..(2517)

<400> SEQUENCE: 1 atg cct cgt cta gac gtc gag aag acc atc gaa gaa ctc tcc cta ggg      48
Met Pro Arg Leu Asp Val Glu Lys Thr Ile Glu Glu Leu Ser Leu Gly
1               5                   10                  15 gag aag gtc gcc ttg acg gcc gga atc gac ttc tgg cac aca gct tcc      96
Glu Lys Val Ala Leu Thr Ala Gly Ile Asp Phe Trp His Thr Ala Ser
            20                  25                  30
```

-continued

| | | |
|---|---|---|
| gtg ccc cgc ctc aac atc cca act ctc cgc atg tcc gat ggc ccc aac<br>Val Pro Arg Leu Asn Ile Pro Thr Leu Arg Met Ser Asp Gly Pro Asn<br>35                          40                       45 | | 144 |
| ggc gtg cgc gga act cgc ttc ttc aac ggc gtc cca gcc gca tgt ttc<br>Gly Val Arg Gly Thr Arg Phe Phe Asn Gly Val Pro Ala Ala Cys Phe<br> 50                        55                      60 | | 192 |
| cct tgt gcc acg gca ctg ggc gca acc tgg gac acc gag ctg ctc cat<br>Pro Cys Ala Thr Ala Leu Gly Ala Thr Trp Asp Thr Glu Leu Leu His<br>65                        70                     75                     80 | | 240 |
| gag att ggt caa ttg atg gga gag gaa tcc att gcc aag ggc tcg cac<br>Glu Ile Gly Gln Leu Met Gly Glu Glu Ser Ile Ala Lys Gly Ser His<br>                    85                     90                     95 | | 288 |
| att att cta ggc ccc acg atc aac acc cag cgg tct ccg ctc gga ggt<br>Ile Ile Leu Gly Pro Thr Ile Asn Thr Gln Arg Ser Pro Leu Gly Gly<br>                 100                    105                  110 | | 336 |
| cgt gga ttc gag tcc ttt gct gag gac ggt gtg ctc tct gga ctc ttg<br>Arg Gly Phe Glu Ser Phe Ala Glu Asp Gly Val Leu Ser Gly Leu Leu<br>115                       120                    125 | | 384 |
| gcc ggt tat atc tcc aag ggt att cag gag aag ggc gtt gcg gcc act<br>Ala Gly Tyr Ile Ser Lys Gly Ile Gln Glu Lys Gly Val Ala Ala Thr<br>        130                    135                    140 | | 432 |
| ctg aag cac ttt gtg tgc aat gac cag gag cat cag cgt atg gct gtt<br>Leu Lys His Phe Val Cys Asn Asp Gln Glu His Gln Arg Met Ala Val<br>145                       150                    155                  160 | | 480 |
| gat agc att gtt acg cag cgg gct ctg cgc gag atc tat ttg ttg ccg<br>Asp Ser Ile Val Thr Gln Arg Ala Leu Arg Glu Ile Tyr Leu Leu Pro<br>                 165                    170                  175 | | 528 |
| ttt caa ttg gcc atg agg att tgc agg acg gct tgt gtt atg aca gct<br>Phe Gln Leu Ala Met Arg Ile Cys Arg Thr Ala Cys Val Met Thr Ala<br>        180                    185                    190 | | 576 |
| tat aac aag gtg aat gga acg cac gtt agt cag aat aag gaa atc atc<br>Tyr Asn Lys Val Asn Gly Thr His Val Ser Gln Asn Lys Glu Ile Ile<br>                 195                    200                  205 | | 624 |
| acg gat atc ttg cgg aag gag tgg gga tgg gat ggg ttg gtt atg agt<br>Thr Asp Ile Leu Arg Lys Glu Trp Gly Trp Asp Gly Leu Val Met Ser<br>210                       215                    220 | | 672 |
| gat tgg ttc ggt acc tac agt acc agt gat gca atc aat gct ggt ttg<br>Asp Trp Phe Gly Thr Tyr Ser Thr Ser Asp Ala Ile Asn Ala Gly Leu<br>225                       230                    235                  240 | | 720 |
| gac ctg gag atg ccg ggc aag aca cgc tgg cgt gga act gct ctg gcg<br>Asp Leu Glu Met Pro Gly Lys Thr Arg Trp Arg Gly Thr Ala Leu Ala<br>                 245                    250                  255 | | 768 |
| cat gcc gtt tct tcg aac gag gtc gct gag ttt gtc atg gat gag cgt<br>His Ala Val Ser Ser Asn Glu Val Ala Glu Phe Val Met Asp Glu Arg<br>        260                    265                    270 | | 816 |
| gtc cgc aat gtg ttg aac ctg gtt aac ttt gtg gat ggc ctg aac atc<br>Val Arg Asn Val Leu Asn Leu Val Asn Phe Val Asp Gly Leu Asn Ile<br>                 275                    280                  285 | | 864 |
| ccg gag aac gcc ccg gag aag gct ctc aac cgg cca cag gac caa gct<br>Pro Glu Asn Ala Pro Glu Lys Ala Leu Asn Arg Pro Gln Asp Gln Ala<br>290                       295                    300 | | 912 |
| ctt ctc cgc cgt gct gcg gcg gag tct gtc gtt ctc atg aag aac gag<br>Leu Leu Arg Arg Ala Ala Ala Glu Ser Val Val Leu Met Lys Asn Glu<br>305                       310                    315                  320 | | 960 |
| gaa gac atc ttg ccc ctg aag aag gag aag tct atc ttg gtt att ggt<br>Glu Asp Ile Leu Pro Leu Lys Lys Glu Lys Ser Ile Leu Val Ile Gly<br>                 325                    330                  335 | | 1008 |
| cct aac tcc aag gtt gcg gcg tac tgc ggc ggt gga tcc gcg tct ttg<br>Pro Asn Ser Lys Val Ala Ala Tyr Cys Gly Gly Gly Ser Ala Ser Leu<br>        340                    345                    350 | | 1056 |

-continued

| | |
|---|---|
| gat gct tat tac act gtc acc cca ttc gag ggt gtc tcg gct cag agc<br>Asp Ala Tyr Tyr Thr Val Thr Pro Phe Glu Gly Val Ser Ala Gln Ser<br>355                                      360                        365 | 1104 |
| aag ggt gag gtc aag ttc tct caa ggt gtc tat tcg cac aag gac ctt<br>Lys Gly Glu Val Lys Phe Ser Gln Gly Val Tyr Ser His Lys Asp Leu<br>370                                      375                        380 | 1152 |
| cct ctc ctt gga ccc ctg ctg aag acc gcc gac ggc aag act ggt ttc<br>Pro Leu Leu Gly Pro Leu Leu Lys Thr Ala Asp Gly Lys Thr Gly Phe<br>385                              390                        395                        400 | 1200 |
| tca ttc aag gta tac aac gag cac cct tcc gag tct aac cgc gaa ctt<br>Ser Phe Lys Val Tyr Asn Glu His Pro Ser Glu Ser Asn Arg Glu Leu<br>                        405                        410                        415 | 1248 |
| atc gag cag ctg cac ctg gtc tcg tcg agc gga ttc cta atg gac tat<br>Ile Glu Gln Leu His Leu Val Ser Ser Ser Gly Phe Leu Met Asp Tyr<br>                    420                        425                        430 | 1296 |
| gtc aac ccc aag atc aag tct ctc acc tac tac gtc gac atg gag ggt<br>Val Asn Pro Lys Ile Lys Ser Leu Thr Tyr Tyr Val Asp Met Glu Gly<br>                435                        440                        445 | 1344 |
| ctc ttc acc ccc gag gaa gac ggt gtc tac gac ttc ggt gtc act gtt<br>Leu Phe Thr Pro Glu Glu Asp Gly Val Tyr Asp Phe Gly Val Thr Val<br>450                                      455                        460 | 1392 |
| gtt ggc acc ggc caa ctg ttc atc gac ggc gag ctc gtc gtt gac aac<br>Val Gly Thr Gly Gln Leu Phe Ile Asp Gly Glu Leu Val Val Asp Asn<br>465                                      470                        475                        480 | 1440 |
| acc aag aac cag cgc cag ggc tcc gcc ttc ttc ggc tcc gct acc gtc<br>Thr Lys Asn Gln Arg Gln Gly Ser Ala Phe Phe Gly Ser Ala Thr Val<br>                    485                        490                        495 | 1488 |
| gaa gag aag ggc tcc aaa gaa ctc aag gcc ggc caa aca tac aag gtt<br>Glu Glu Lys Gly Ser Lys Glu Leu Lys Ala Gly Gln Thr Tyr Lys Val<br>              500                        505                        510 | 1536 |
| ctc ttc cag ttc ggc aca gcc cct acc tcc gac ctc gat acc cgc ggc<br>Leu Phe Gln Phe Gly Thr Ala Pro Thr Ser Asp Leu Asp Thr Arg Gly<br>            515                        520                        525 | 1584 |
| gtg gta gtc ttc gga ccc ggt ggc ttc cgc ttc gga gcc agc cgt cgc<br>Val Val Phe Gly Pro Gly Gly Phe Arg Phe Gly Ala Ser Arg Arg<br>      530                        535                        540 | 1632 |
| gtc ggc cag gaa gag ctc atc tcc aac gcc gtc aag ctc gcc tcc gag<br>Val Gly Gln Glu Glu Leu Ile Ser Asn Ala Val Lys Leu Ala Ser Glu<br>545                                    550                        555                        560 | 1680 |
| gcc gaa caa gta gtc gtc ttc gcc ggt ctg act agc gaa tgg gaa acc<br>Ala Glu Gln Val Val Val Phe Ala Gly Leu Thr Ser Glu Trp Glu Thr<br>                    565                        570                        575 | 1728 |
| gag ggc tac gac cgc gac cac atg gac ctt ccc ccc ggc agc gac gag<br>Glu Gly Tyr Asp Arg Asp His Met Asp Leu Pro Pro Gly Ser Asp Glu<br>              580                        585                        590 | 1776 |
| atg atc tcg cgc gtg ctg gac gtc aac ccg aac gcc gtc gtg gtc att<br>Met Ile Ser Arg Val Leu Asp Val Asn Pro Asn Ala Val Val Val Ile<br>            595                        600                        605 | 1824 |
| cag agc ggc acc cca gtg acc atg cca tgg gcc aac aag acc aag gct<br>Gln Ser Gly Thr Pro Val Thr Met Pro Trp Ala Asn Lys Thr Lys Ala<br>610                                      615                        620 | 1872 |
| ctc cta cac gcc tgg ttc ggc ggt aac gag tgc ggt aac ggt atc gcg<br>Leu Leu His Ala Trp Phe Gly Gly Asn Glu Cys Gly Asn Gly Ile Ala<br>625                                      630                        635                        640 | 1920 |
| gac gtg ctc tac ggc gac gtc aac ccc tcc ggc aag ctg ccc att act<br>Asp Val Leu Tyr Gly Asp Val Asn Pro Ser Gly Lys Leu Pro Ile Thr<br>                        645                        650                        655 | 1968 |
| ttc ccc gta cgt ctg cag gac aac ccc agc tac gtc aac ttt cgt tcc<br>Phe Pro Val Arg Leu Gln Asp Asn Pro Ser Tyr Val Asn Phe Arg Ser | 2016 |

```
                     660                     665                     670
gag cgc ggc cgt gtc ctc tac ggt gaa gac gtc tac gtc gga tac cgc        2064
Glu Arg Gly Arg Val Leu Tyr Gly Glu Asp Val Tyr Val Gly Tyr Arg
            675                     680                     685 tac tac gaa aag gtc gat ctg gcc cct ctc ttc ccc ttc ggc cac ggt        2112
Tyr Tyr Glu Lys Val Asp Leu Ala Pro Leu Phe Pro Phe Gly His Gly
        690                     695                     700 ctc tcc tac acc acc ttc acc cgc tcc gac ctg acc ctc acc acc act        2160
Leu Ser Tyr Thr Thr Phe Thr Arg Ser Asp Leu Thr Leu Thr Thr Thr
705                     710                     715                     720 ccc gag aag ccc cag tac gaa gaa agc ggc gag ccc atc acc gca acc        2208
Pro Glu Lys Pro Gln Tyr Glu Glu Ser Gly Glu Pro Ile Thr Ala Thr
                725                     730                     735 gtc acg gtg acc aac acc ggc aag gtc gcc ggt gca gag atc gtc cag        2256
Val Thr Val Thr Asn Thr Gly Lys Val Ala Gly Ala Glu Ile Val Gln
            740                     745                     750 ctc tgg gtc gct ccc ccg gca acg gaa gtc aac cgt ccc gtc cgc gaa        2304
Leu Trp Val Ala Pro Pro Ala Thr Glu Val Asn Arg Pro Val Arg Glu
        755                     760                     765 ctc aag gga ttc act aag gtc ttc ctg cag cct ggt gag cag aag aag        2352
Leu Lys Gly Phe Thr Lys Val Phe Leu Gln Pro Gly Glu Gln Lys Lys
770                     775                     780 gtc gag atc gtc gtg gag aag aag ctg gcg acg agt tgg ttc gac gag        2400
Val Glu Ile Val Val Glu Lys Lys Leu Ala Thr Ser Trp Phe Asp Glu
785                     790                     795                     800 atg cgc gag aag tgg gcg tcc gag aaa ggc gag tat gag gtt ctt gta        2448
Met Arg Glu Lys Trp Ala Ser Glu Lys Gly Glu Tyr Glu Val Leu Val
                805                     810                     815 act ggt act ggc gag ggt gtt ctt aag tcg tcc ttc aag gtc gag aag        2496
Thr Gly Thr Gly Glu Gly Val Leu Lys Ser Ser Phe Lys Val Glu Lys
            820                     825                     830 act cgc tac tgg ttg ggt ctg tga                                        2520
Thr Arg Tyr Trp Leu Gly Leu
        835

<210> SEQ ID NO 2
<211> LENGTH: 839
<212> TYPE: PRT
<213> ORGANISM: Aspergillus oryzae

<400> SEQUENCE: 2

Met Pro Arg Leu Asp Val Glu Lys Thr Ile Glu Glu Leu Ser Leu Gly
1               5                   10                  15

Glu Lys Val Ala Leu Thr Ala Gly Ile Asp Phe Trp His Thr Ala Ser
            20                  25                  30

Val Pro Arg Leu Asn Ile Pro Thr Leu Arg Met Ser Asp Gly Pro Asn
        35                  40                  45

Gly Val Arg Gly Thr Arg Phe Phe Asn Gly Val Pro Ala Ala Cys Phe
    50                  55                  60

Pro Cys Ala Thr Ala Leu Gly Ala Thr Trp Asp Thr Glu Leu Leu His
65                  70                  75                  80

Glu Ile Gly Gln Leu Met Gly Glu Glu Ser Ile Ala Lys Gly Ser His
                85                  90                  95

Ile Ile Leu Gly Pro Thr Ile Asn Thr Gln Arg Ser Pro Leu Gly Gly
            100                 105                 110

Arg Gly Phe Glu Ser Phe Ala Glu Asp Gly Val Leu Ser Gly Leu Leu
        115                 120                 125

Ala Gly Tyr Ile Ser Lys Gly Ile Gln Glu Lys Gly Val Ala Ala Thr
```

-continued

```
            130                 135                 140
Leu Lys His Phe Val Cys Asn Asp Gln Glu His Gln Arg Met Ala Val
145                 150                 155                 160

Asp Ser Ile Val Thr Gln Arg Ala Leu Arg Glu Ile Tyr Leu Leu Pro
                165                 170                 175

Phe Gln Leu Ala Met Arg Ile Cys Arg Thr Ala Cys Val Met Thr Ala
            180                 185                 190

Tyr Asn Lys Val Asn Gly Thr His Val Ser Gln Asn Lys Glu Ile Ile
            195                 200                 205

Thr Asp Ile Leu Arg Lys Glu Trp Gly Trp Asp Gly Leu Val Met Ser
210                 215                 220

Asp Trp Phe Gly Thr Tyr Ser Thr Ser Asp Ala Ile Asn Ala Gly Leu
225                 230                 235                 240

Asp Leu Glu Met Pro Gly Lys Thr Arg Trp Arg Gly Thr Ala Leu Ala
                245                 250                 255

His Ala Val Ser Ser Asn Glu Val Ala Glu Phe Val Met Asp Glu Arg
            260                 265                 270

Val Arg Asn Val Leu Asn Leu Val Asn Phe Val Asp Gly Leu Asn Ile
            275                 280                 285

Pro Glu Asn Ala Pro Glu Lys Ala Leu Asn Arg Pro Gln Asp Gln Ala
290                 295                 300

Leu Leu Arg Arg Ala Ala Ala Glu Ser Val Val Leu Met Lys Asn Glu
305                 310                 315                 320

Glu Asp Ile Leu Pro Leu Lys Lys Glu Lys Ser Ile Leu Val Ile Gly
                325                 330                 335

Pro Asn Ser Lys Val Ala Ala Tyr Cys Gly Gly Ser Ala Ser Leu
            340                 345                 350

Asp Ala Tyr Tyr Thr Val Thr Pro Phe Glu Gly Val Ser Ala Gln Ser
            355                 360                 365

Lys Gly Glu Val Lys Phe Ser Gln Gly Val Tyr Ser His Lys Asp Leu
370                 375                 380

Pro Leu Leu Gly Pro Leu Leu Lys Thr Ala Asp Gly Lys Thr Gly Phe
385                 390                 395                 400

Ser Phe Lys Val Tyr Asn Glu His Pro Ser Glu Ser Asn Arg Glu Leu
                405                 410                 415

Ile Glu Gln Leu His Leu Val Ser Ser Gly Phe Leu Met Asp Tyr
            420                 425                 430

Val Asn Pro Lys Ile Lys Ser Leu Thr Tyr Tyr Val Asp Met Glu Gly
            435                 440                 445

Leu Phe Thr Pro Glu Glu Asp Gly Val Tyr Asp Phe Gly Val Thr Val
450                 455                 460

Val Gly Thr Gly Gln Leu Phe Ile Asp Gly Glu Leu Val Val Asp Asn
465                 470                 475                 480

Thr Lys Asn Gln Arg Gln Gly Ser Ala Phe Phe Gly Ser Ala Thr Val
                485                 490                 495

Glu Glu Lys Gly Ser Lys Glu Leu Lys Ala Gly Gln Thr Tyr Lys Val
            500                 505                 510

Leu Phe Gln Phe Gly Thr Ala Pro Thr Ser Asp Leu Asp Thr Arg Gly
            515                 520                 525

Val Val Val Phe Gly Pro Gly Gly Phe Arg Phe Gly Ala Ser Arg Arg
530                 535                 540

Val Gly Gln Glu Glu Leu Ile Ser Asn Ala Val Lys Leu Ala Ser Glu
545                 550                 555                 560
```

```
Ala Glu Gln Val Val Phe Ala Gly Leu Thr Ser Glu Trp Glu Thr
                565                 570                 575

Glu Gly Tyr Asp Arg Asp His Met Asp Leu Pro Pro Gly Ser Asp Glu
            580                 585                 590

Met Ile Ser Arg Val Leu Asp Val Asn Pro Asn Ala Val Val Ile
        595                 600                 605

Gln Ser Gly Thr Pro Val Thr Met Pro Trp Ala Asn Lys Thr Lys Ala
    610                 615                 620

Leu Leu His Ala Trp Phe Gly Gly Asn Glu Cys Gly Asn Gly Ile Ala
625                 630                 635                 640

Asp Val Leu Tyr Gly Asp Val Asn Pro Ser Gly Lys Leu Pro Ile Thr
            645                 650                 655

Phe Pro Val Arg Leu Gln Asp Asn Pro Ser Tyr Val Asn Phe Arg Ser
            660                 665                 670

Glu Arg Gly Arg Val Leu Tyr Gly Glu Asp Val Tyr Val Gly Tyr Arg
        675                 680                 685

Tyr Tyr Glu Lys Val Asp Leu Ala Pro Leu Phe Pro Phe Gly His Gly
    690                 695                 700

Leu Ser Tyr Thr Thr Phe Thr Arg Ser Asp Leu Thr Leu Thr Thr Thr
705                 710                 715                 720

Pro Glu Lys Pro Gln Tyr Glu Glu Ser Gly Glu Pro Ile Thr Ala Thr
            725                 730                 735

Val Thr Val Thr Asn Thr Gly Lys Val Ala Gly Ala Glu Ile Val Gln
            740                 745                 750

Leu Trp Val Ala Pro Pro Ala Thr Glu Val Asn Arg Pro Val Arg Glu
        755                 760                 765

Leu Lys Gly Phe Thr Lys Val Phe Leu Gln Pro Gly Glu Gln Lys Lys
    770                 775                 780

Val Glu Ile Val Val Glu Lys Lys Leu Ala Thr Ser Trp Phe Asp Glu
785                 790                 795                 800

Met Arg Glu Lys Trp Ala Ser Glu Lys Gly Glu Tyr Glu Val Leu Val
            805                 810                 815

Thr Gly Thr Gly Glu Val Leu Lys Ser Ser Phe Lys Val Glu Lys
            820                 825                 830

Thr Arg Tyr Trp Leu Gly Leu
        835

<210> SEQ ID NO 3
<211> LENGTH: 2571
<212> TYPE: DNA
<213> ORGANISM: Aspergillus oryzae

<400> SEQUENCE: 3
atgcctcgtc tagacgtcga aagaccatc gaagaactct ccctagggga aaggtcgcc       60 ttgacggccg gtaagtcaaa aacccacgat cgcaagagaa agaaatgct aagaatccca     120 ggaatcgact tctggcacac agcttccgtg ccccgcctca acatcccaac tctccgcatg   180
tccgatggcc ccaacggcgt gcgcggaact cgcttcttca cggcgtccc agccgcatgt    240 ttcccttgtg ccacggcact gggcgcaacc tgggacaccg agctgctcca tgagattggt   300
caattgatgg gagaggaatc cattgccaag ggctcgcaca ttattctagg ccccacgatc   360
aacacccagc ggtctccgct cggaggtcgt ggattcgagt cctttgctga ggacggtgtg   420
ctctctggac tcttggccgg ttatatctcc aagggtattc aggagaaggg cgttgcggcc   480
```

```
actctgaagc actttgtgtg caatgaccag gagcatcagc gtatggctgt tgatagcatt    540
gttacgcagc gggctctgcg cgagatctat ttgttgccgt ttcaattggc catgaggatt    600
tgcaggacgg cttgtgttat gacagcttat aacaaggtga atggaacgca cgttagtcag    660
aataaggaaa tcatcacgga tatcttgcgg aaggagtggg gatgggatgg gttggttatg    720
agtgattggt tcggtaccta cagtaccagt gatgcaatca atgctggttt ggacctggag    780
atgccgggca agacacgctg gcgtggaact gctctggcgc atgccgtttc ttcgaacgag    840
gtcgctgagt ttgtcatgga tgagcgtgtc cgcaatgtgt tgaacctggt taactttgtg    900
gatggcctga acatcccgga gaacgccccg gagaaggctc tcaaccggcc acaggaccaa    960
gctcttctcc gccgtgctgc ggcggagtct gtcgttctca tgaagaacga ggaagacatc    1020
ttgcccctga gaaggagaa gtctatcttg gttattggtc ctaactccaa ggttgcggcg    1080
tactgcggcg gtggatccgc gtctttggat gcttattaca ctgtcacccc attcgagggt    1140
gtctcggctc agagcaaggg tgaggtcaag ttctctcaag gtgtctattc gcacaaggac    1200
cttcctctcc ttggacccct gctgaagacc gccgacggca agactggttt ctcattcaag    1260
gtatacaacg agcacccttc cgagtctaac cgcgaactta tcgagcagct gcacctggtc    1320
tcgtcgagcg gattcctaat ggactatgtc aaccccaaga tcaagtctct cacctactac    1380
gtcgacatgg agggtctctt cacccccgag gaagacggtg tctacgactt cggtgtcact    1440
gttgttggca ccggccaact gttcatcgac ggcgagctcg tcgttgacaa caccaagaac    1500
cagcgccagg gctccgcctt cttcggctcc gctaccgtcg aagagaaggg ctccaaagaa    1560
ctcaaggccg gccaaacata caaggttctc ttccagttcg gcacagcccc tacctccgac    1620
ctcgataccc gcggcgtggt agtcttcgga cccggtggct ccgcttcgg agccagccgt    1680 cgcgtcggcc aggaagagct catctccaac gccgtcaagc tcgcctccga ggccgaacaa    1740
gtagtcgtct cgccggtct gactagcgaa tgggaaaccg agggctacga ccgcgaccac    1800
atggaccttc ccccggcag cgacgagatg atctcgcgcg tgctggacgt caaccccgaac    1860 gccgtcgtgg tcattcagag cggcacccca gtgaccatgc catgggccaa caagaccaag    1920
gctctcctac acgcctggtt cggcggtaac gagtgcggta acggtatcgc ggacgtgctc    1980
tacggcgacg tcaacccctc cggcaagctg cccattactt tccccgtacg tctgcaggac    2040
aaccccagct acgtcaactt tcgttccgag gcgccggccgtg tcctctacgg tgaagacgtc    2100
tacgtcggat accgctacta cgaaaaggtc gatctggccc ctctcttccc cttcggccac    2160
ggtctctcct acaccacctt cacccgctcc gacctgaccc tcaccaccac tcccgagaag    2220
ccccagtacg aagaaagcgg cgagcccatc accgcaaccg tcacggtgac caacaccggc    2280
aaggtcgccg gtgcagagat cgtccagctc tgggtcgctc cccggcaac ggaagtcaac    2340 cgtcccgtcc gcgaactcaa gggattcact aaggtcttcc tgcagcctgg tgagcagaag    2400
aaggtcgaga tcgtcgtgga gaagaagctg gcgacgagtt ggttcgacga gatgcgcgag    2460
aagtgggcgt ccgagaaagg cgagtatgag gttcttgtaa ctggtactgg cgagggtgtt    2520
cttaagtcgt ccttcaaggt cgagaagact cgctactggt tgggtctgtg a    2571
```

<210> SEQ ID NO 4
<211> LENGTH: 23
<212> TYPE: DNA
<213> ORGANISM: Artificial Sequence
<220> FEATURE:
<223> OTHER INFORMATION: AOBGL11-F

<400> SEQUENCE: 4

```
atgcctcgtc tagacgtcga gaa                                        23
```

<210> SEQ ID NO 5
<211> LENGTH: 22
<212> TYPE: DNA
<213> ORGANISM: Artificial Sequence
<220> FEATURE:
<223> OTHER INFORMATION: AOBGL11-R

<400> SEQUENCE: 5

```
tcacagaccc aaccagtagc ga                                         22
```